US010937296B1

United States Patent
Kukreja et al.

(10) Patent No.: US 10,937,296 B1
(45) Date of Patent: Mar. 2, 2021

(54) SYSTEM AND METHOD TO MANAGE SAFE PHYSICAL DISTANCING BETWEEN ENTITIES

(71) Applicant: Unityband, LLC, Fort Lauderdale, FL (US)

(72) Inventors: Rishi Kukreja, Fort Lauderdale, FL (US); Gary Barbour, Fort Lauderdale, FL (US); Sunny Kapoor, Fort Lauderdale, FL (US); Soumendra Mahapatra, Fort Lauderdale, FL (US)

(73) Assignee: Unityband, LLC, Fort Lauderdale, FL (US)

( * ) Notice: Subject to any disclaimer, the term of this patent is extended or adjusted under 35 U.S.C. 154(b) by 0 days.

(21) Appl. No.: 16/914,961

(22) Filed: Jun. 29, 2020

Related U.S. Application Data

(60) Provisional application No. 63/010,044, filed on Apr. 14, 2020.

(51) Int. Cl.
*G08B 21/02* (2006.01)
*G16H 40/67* (2018.01)
(Continued)

(52) U.S. Cl.
CPC ......... *G08B 21/02* (2013.01); *G06K 7/10366* (2013.01); *G08B 21/245* (2013.01); *G08B 25/10* (2013.01); *G16H 10/20* (2018.01); *G16H 10/40* (2018.01); *G16H 10/65* (2018.01); *G16H 40/67* (2018.01); *G16H 50/20* (2018.01); *G16H 50/30* (2018.01); *G16H 50/80* (2018.01); *H04W 12/06* (2013.01); *G06Q 50/01* (2013.01)

(58) Field of Classification Search
CPC ...... G08B 21/02; G08B 21/245; G08B 25/10; G16H 40/67; G16H 10/40; G16H 50/30; G16H 50/20; G16H 50/80; G16H 10/20; G16H 10/65; H04W 12/06; G06F 1/163; G06Q 50/01; G06Q 20/321; G01K 17/185; G06K 7/10366; G06K 7/10396
See application file for complete search history.

(56) References Cited

U.S. PATENT DOCUMENTS 6,255,951 B1 * 7/2001 De La Huerga ....... G04G 21/04
340/573.1
8,237,558 B2 * 8/2012 Seyed Momen ..... G01S 1/7034
340/539.11
(Continued)

*Primary Examiner* — Rufus C Point
(74) *Attorney, Agent, or Firm* — Rahman LLC

(57) ABSTRACT

A wearable electronic device, system and method to manage safe physical distancing between a first entity and one or more proximate entities for limiting pathogenic exposure therebetween, includes obtaining an identity attribute associated with a wearable electronic device worn by the first entity; authenticating a first entity electronic device or a computing device; receiving, at a centralized server, a first set of data packets related to a status query associated with the one or more health attributes of the first entity; computing a status information, in response to the status query; transmitting a second set of data packets related to the computed status information; and transmitting the obtained status information, to provide one or more unique alerts on the wearable electronic device of the one or more health attributes of the first entity to the one or more proximate entities.

21 Claims, 11 Drawing Sheets

(51) Int. Cl.
*G16H 50/30* (2018.01)
*G16H 10/20* (2018.01)
*G16H 10/40* (2018.01)
*G16H 10/65* (2018.01)
*G16H 50/20* (2018.01)
*G06K 7/10* (2006.01)
*H04W 12/06* (2009.01)
*G08B 25/10* (2006.01)
*G08B 21/24* (2006.01)
*G16H 50/80* (2018.01)
*G06Q 50/00* (2012.01)

(56) References Cited

U.S. PATENT DOCUMENTS

| | | | |
|---|---|---|---|
| 8,924,248 B2 * | 12/2014 | Tropper | A61B 5/6828 705/14.22 |
| 9,750,433 B2 | 9/2017 | Hu et al. | |
| 9,861,314 B2 | 1/2018 | Haverinen et al. | |
| D811,260 S | 2/2018 | Koskinen | |
| 9,996,678 B2 * | 6/2018 | Johnson | H04W 4/80 |
| 9,997,945 B2 | 6/2018 | Kallunki et al. | |
| 10,105,095 B2 | 10/2018 | Kinnunen | |
| 10,108,151 B2 * | 10/2018 | Cardinali | G04G 21/00 |
| 10,210,735 B2 * | 2/2019 | Narisada | G16H 50/80 |
| 10,212,136 B1 * | 2/2019 | Gehret | H04W 12/06 |
| 10,362,769 B1 * | 7/2019 | Kartoun | A61B 5/0022 |
| 10,401,800 B2 * | 9/2019 | Cardinali | G04G 9/0064 |
| 10,467,679 B1 * | 11/2019 | Toumazou | A61B 5/1118 |
| D884,502 S | 5/2020 | Kivela et al. | |
| 10,714,212 B2 * | 7/2020 | Chen | G16H 40/63 |
| 2002/0068873 A1 * | 6/2002 | Nissila | A61B 5/681 600/509 |
| 2002/0084904 A1 * | 7/2002 | De La Huerga | G16H 10/65 340/573.1 |
| 2003/0187615 A1 * | 10/2003 | Epler | G06N 20/00 702/181 |
| 2009/0012818 A1 * | 1/2009 | Rodgers | G06Q 50/24 705/3 |
| 2009/0299150 A1 * | 12/2009 | Alberte, Jr. | A61B 5/74 600/300 |
| 2011/0193703 A1 * | 8/2011 | Payton | G08B 21/245 340/573.1 |
| 2014/0055619 A1 * | 2/2014 | Holland | H04N 7/181 348/159 |
| 2014/0099614 A1 | 4/2014 | Hu et al. | |
| 2014/0183269 A1 * | 7/2014 | Glaser | G06Q 20/34 235/492 |
| 2014/0205155 A1 * | 7/2014 | Chung | G06Q 50/26 382/115 |
| 2014/0304381 A1 * | 10/2014 | Savolainen | H04L 41/0806 709/222 |
| 2014/0349257 A1 * | 11/2014 | Connor | G16H 20/60 434/127 |
| 2014/0363797 A1 * | 12/2014 | Hu | G09B 19/0092 434/236 |
| 2015/0164430 A1 | 6/2015 | Hu et al. | |
| 2015/0186609 A1 * | 7/2015 | Utter, II | A61B 5/1123 600/301 |
| 2015/0261996 A1 * | 9/2015 | Kim | H04N 5/23218 348/14.03 |
| 2015/0279168 A1 * | 10/2015 | Avrahami | G06F 1/1677 340/539.11 |
| 2015/0294595 A1 | 10/2015 | Hu et al. | |
| 2016/0080936 A1 * | 3/2016 | Rachuri | H04W 12/0605 726/7 |
| 2016/0085331 A1 * | 3/2016 | Kubo | G16H 40/63 345/173 |
| 2016/0132652 A1 * | 5/2016 | Chapman Bates | G06F 19/00 706/11 |
| 2016/0140870 A1 * | 5/2016 | Connor | G01N 21/255 356/51 |
| 2016/0366524 A1 * | 12/2016 | Holmes | G06K 7/1417 |
| 2017/0045918 A1 * | 2/2017 | Han | G02F 1/13318 |
| 2017/0199979 A1 * | 7/2017 | Reiner | G06F 19/324 |
| 2017/0273584 A1 * | 9/2017 | Huang | A61B 5/04085 |
| 2017/0300648 A1 * | 10/2017 | Charlap | G16H 50/30 |
| 2018/0042540 A1 | 2/2018 | Kinnunen et al. | |
| 2018/0103902 A1 | 4/2018 | Haverinen et al. | |
| 2018/0151061 A1 * | 5/2018 | Lauren | G04G 21/04 |
| 2018/0174686 A1 * | 6/2018 | Zaphrir | G16H 10/60 |
| 2018/0182193 A1 * | 6/2018 | Spittle | G06Q 20/321 |
| 2018/0249312 A1 * | 8/2018 | Roh | H04W 12/0608 |
| 2018/0277957 A1 * | 9/2018 | Geist | H01Q 1/243 |
| 2019/0086875 A1 * | 3/2019 | Cardinali | G04G 9/0064 |
| 2019/0165933 A1 * | 5/2019 | Tomisawa | H04L 9/0866 |
| 2019/0341798 A1 | 11/2019 | Jarvela et al. | |
| 2019/0341918 A1 | 11/2019 | Jarvela et al. | |
| 2019/0349367 A1 * | 11/2019 | Chang | H04W 12/0605 |
| 2020/0090486 A1 | 3/2020 | Laakkonen et al. | |
| 2020/0143027 A1 * | 5/2020 | Toumazou | H04W 12/06 |
| 2020/0168070 A1 * | 5/2020 | Bender | G16H 80/00 |
| 2020/0204526 A1 * | 6/2020 | Gehret | H04L 63/0428 |

* cited by examiner

SYSTEM AND METHOD TO MANAGE SAFE PHYSICAL DISTANCING BETWEEN ENTITIES

CROSS-REFERENCE TO RELATED APPLICATIONS

This application claims priority to U.S. Provisional Patent Application No. 63/010,044 filed on Apr. 14, 2020, the complete disclosure of which, in its entirety, is hereby incorporated by reference.

BACKGROUND

Technical Field

The embodiments herein generally relate to health status detection and access control, and more particular to a comprehensive, integrated system and method to facilitate controlled detection of health status, access to facilities and services to track exposure, limit access to, and manage interactions to facilitate safe physical distancing between entities.

Description of the Related Art

Public places may require the presence of people in large numbers. In these situations, there may be high chances of each individual coming in close contact with another person or with common objects touched by another person. In a normal scenario, this would be relatively safe; however, in situations involving pandemic and other high risk scenarios such as coronavirus pandemic (COVID), caused by acute respiratory syndrome coronavirus 2 (SARS-CoV-2), it becomes highly significant to limit pathogenic exposure by avoiding any contact between two persons or limiting the interaction therebetween in a public place or other social gatherings. Such contactless interaction may require a safe physical distancing between individuals, as well as avoiding contact with commonly accessed objects such as doors, seats, and the like, for limiting exposure and further spreading of the pathogens. Further, access to places witnessing public gatherings such as airports, stations, restaurants, theaters, cinemas, schools, offices, government buildings, malls, stadiums, supermarkets, stores, clubs, and the like, would need systemized management to allow controlled access or entry therein based on an assessment of risk caused by any person to other individuals. In such cases, a criterion may be prescribed based on health status, travel history, employment, or daily interaction routine of individuals to manage access, however, such a methodology may not be possible by the conventional systems or methods.

One of the challenges that such assessed risk-based entry may pose is that it may require that every individual be tested for any pathogenic infection or at least screened for the symptoms caused by the infection. While testing of each individual may be practically impossible, the screening for symptoms, though practically possible, may be ineffective as even an infected person may not show symptoms in an incubation period, which is the period between pathogenic exposure and the occurrence of symptoms, and may be allowed access thereby risking other individuals. Further, even on an individual level, there may be a sense of fear or discomfort to approach public places in a pandemic, as it may be practically impossible to not accidently come in contact with an infected person or a surface containing pathogens, thus highlighting the need to offer greater mental satisfaction to individuals in a society who may require to access public places in a pandemic. Furthermore, it may be a tedious task to keep track of the interaction(s) of an infected person with other individuals, before the occurrence of symptoms for contact tracing.

SUMMARY

In view of the foregoing, an embodiment herein provides a wearable electronic device to indicate one or more health attributes of a first entity to facilitate safe physical distancing between the first entity and one or more proximate entities for limiting pathogenic exposure, the device comprising a housing to attach to the first entity; one or more sensors disposed in the housing and to sense the one or more health attributes of the first entity; a transceiver associated with an identifier tag and to enable communication of the one or more sensors with at least one of a first entity electronic device associated with the first entity and a computing device; and an indicator integrated with the housing to facilitate the safe physical distancing between the first entity and the one or more proximate entities for limiting pathogenic exposure therebetween by providing one or more unique alerts of the one or more health attributes of the first entity to the one or more proximate entities, wherein the one or more unique alerts indicate a status of the one of more health attributes.

The transceiver may comprise a Bluetooth® low energy (BLE) transceiver, and wherein the identifier tag comprises any of a radio frequency identification (RFID) tag and Bluetooth® Low Energy (BLE) identifier. The one or more sensors may comprise any of a pedometer, an accelerometer, light sensor, optical sensor, infrared sensor and a temperature sensor, and wherein the indicator comprises at least one of a visual indicator, a light indicator, a haptic indicator, and a sound indicator. The device may comprise a power source to power one or more electrical components of the wearable electronic device. The indicator may comprise a light emitting diode (LED) indicator, wherein the LED indicator is disposed within the housing of the wearable electronic device, and is associated with one or more illumination zones on the housing, to visually display the one or more unique alerts, and wherein each illumination zone is associated with the one or more health attributes of the first entity.

Another embodiment provides a system to manage safe physical distancing between a first entity and one or more proximate entities, the system comprising a wearable electronic device comprising: one or more sensors to sense one or more health attributes of the first entity; a transceiver to enable communication of the wearable electronic device with at least one of a first entity electronic device associated with the first entity and a computing device; and an indicator coupled to the one or more sensors and the transceiver to provide one or more unique alerts of the one or more health attributes of the first entity to the one or more proximate entities, wherein the one or more unique alerts indicate a status of the one of more health attributes; a centralized server comprising one or more processors coupled with a memory, the memory storing instructions which when executed by the one or more processors cause the system to: receive, from the first entity electronic device or the computing device, a first set of data packets related to a status query associated with the one or more health attributes of the first entity; compute a status information, in response to the status query based on the one or more health attributes stored in a database of the centralized server, wherein the one or more health attributes is updated in the database using one or more inputs from any one of an external database and the first entity electronic device, wherein the first entity electronic device provides the inputs to the database based on a manual entry by the first entity or automatically through the one or more sensors of the wearable electronic device; and transmit to the first entity electronic device or the computing device, a second set of data packets related to the status information, in response to the status query. The system further comprises one or more computing devices communicably coupled to centralized server, and to transmit, using a communication interface, to the wearable electronic device, the obtained status information from the centralized server, to actuate an indicator of the wearable electronic device, to provide one or more unique alerts to manage the safe physical distancing between the first entity and the one or more proximate entities for limiting pathogenic exposure therebetween.

Another embodiment provides a method for indicating one or more health attributes of a first entity on a wearable electronic device to facilitate safe physical distancing between the first entity and one or more proximate entities for limiting pathogenic exposure, the method comprising obtaining, using a computing device or a first entity electronic device associated with the first entity, an identity attribute associated with a wearable electronic device worn by the first entity; authenticating, based on the obtained identity attribute, the first entity electronic device or the computing device, to access a database of a centralized server; receiving, at the centralized server, from the first entity electronic device or the computing device, a first set of data packets related to a status query associated with the one or more health attributes of the first entity; computing, at one or more processors of the centralized server, a status information, in response to the status query based on the one or more health attributes of the first entity stored in the database of the centralized server, wherein the one or more health attributes is updated in the database using one or more inputs from any one of an external database or the first entity electronic device, and wherein the first entity electronic device provides the inputs to the database of the centralized server, based on a manual entry in the first entity electronic device by the first entity or through one or more sensors of the wearable electronic device; transmitting, by the one or more processors of the centralized server, to the first entity electronic device or the computing device, a second set of data packets related to the computed status information; and transmitting, from the first entity electronic device or the computing device, using a communication interface, to the wearable electronic device, the obtained status information associated with the one or more health attributes of the first entity, to actuate an indicator of the wearable electronic device, to provide one or more unique alerts of the one or more health attributes of the first entity to the one or more proximate entities, wherein the one or more unique alerts indicate a status of the one of more health attributes to facilitate the safe physical distancing between the first entity and the one or more proximate entities for limiting pathogenic exposure therebetween.

The communication interface may comprise a transceiver on the wearable electronic device, and the identity attribute comprises a Bluetooth® Low Energy (BLE) identifier associated with the transceiver, and wherein the authenticating is performed using a two-step authentication process. The method may comprise scanning a radio frequency identification (RFID) tag on the wearable electronic device to access a RFID code present therein for obtaining the Bluetooth® Low Energy (BLE) identifier associated with the transceiver. The one or more unique alerts may be visually displayed on a light emitting diode (LED) indicator attached to the wearable electronic device to create one or more illumination zones on the wearable electronic device, and wherein each illumination zone is associated with the one or more health attributes of the first entity.

A first illumination zone of the one or more illumination zones may indicate a first health attribute of the one or more health attributes, wherein the first health attribute comprises direct information related to a result of testing the first entity for checking pathogenic infection, wherein the result is selected from infected and active, infected and inactive, and non-infected, and wherein the testing is performed to check the pathogenic infection related to acute respiratory syndrome coronavirus 2 (SARS-CoV-2). A second illumination zone of the one or more illumination zones may indicate a second health attribute of the one or more health attributes, wherein the second health attribute is obtained as the inputs from any of the manual entry by the first entity on the first entity electronic device or automatically through the one or more sensors of the wearable electronic device, and wherein the inputs are related to presence of a condition selected from fever, cough, shortness of breath, tiredness, body ache, muscle ache, headache, nausea, sore throat, and runny nose. A third illumination zone of the one or more illumination zones may indicate a third health attribute of the one or more health attributes, and wherein the third health attribute is associated with a user profile data including a risk assessment of the pathogenic exposure to the first entity, risk assessment of the pathogenic exposure to the one or more proximate entities posed by the first entity, and an ability of the first entity to socialize with the one or more proximate entities with a minimum risk of the pathogenic exposure.

The user profile data may comprise physical attributes and social attributes, wherein the physical attributes comprise any of age, body weight, body height, pre-existing health condition and daily routine details, and wherein the social attributes include a record of interaction of the first entity with the one or more proximate entities, degree of contact of the first entity with the one or more proximate entities, distance travelled by the first entity from a home location to an outside location, a range of area covering maximum distance travelled over a time period around the home location, and wherein the social attributes is computed, by the one or more processors of the centralized server, to calculate at least one score selected from a social distancing score, a direct social score, a risk receivable score, a risk transferrable score, and a total risk factor score. The record of interaction of the first entity with the one or more proximate entities may be updated on the first entity electronic device, wherein the record comprises a timestamp of the interaction and the distance sensed between the wearable electronic device worn by the first entity and a second wearable electronic device worn by the one or more proximate entities.

The method may facilitate safe physical distancing between a first group of entities comprising the first entity, and a second group comprising the one or more proximate entities, wherein the first group comprises a closed group and each member of the first group uses a separate wearable electronic device, wherein the first entity is allowed to interact with each member of the first group without the safe physical distancing, and wherein the method facilitates updating the database by tracking of the separate wearable electronic devices of the first group to record number of the members in the first group interacting with the first entity, duration of stay of the first entity in the first group without any interaction with the second group and health status information of each of the member in the first group.

The method may facilitate, using the one or more unique alerts, to enable alerting the first entity to maintain the safe physical distancing from the one or more proximate entities, alerting the first entity regarding frequency or duration of hand washing, alerting the first entity on face touching movement, and alerting the first entity based on location of movement, when approaching an area of relatively higher pathogenic exposure. The wearable electronic device of the first entity may communicate, using the communication interface, with a third wearable electronic device worn by the one of the proximate entities and share the status information with each other, to visibly indicate the one or more health attributes. The wearable electronic device of the first entity may maintain a record of interaction within a specified distance between the wearable electronic device of the first entity and wearable electronic devices of the proximate entities over a definite time duration to enable contact tracing. The wearable electronic device of the first entity, upon encountering a third wearable electronic device worn by one of the proximate entities, may excite the third wearable electronic device, using the first entity electronic device or the computing device, to provide the one or more unique alerts associated with one or more health attributes of the proximate entity.

Another embodiment provides a non-transitory computer readable storage medium storing one or more sequences of instructions, which when executed by one or more processors, causes indicating one or more health attributes of a first entity on a wearable electronic device to facilitate safe physical distancing between the first entity and one or more proximate entities for limiting pathogenic exposure, by performing a method comprising receiving, at a centralized server, from a first entity electronic device associated with the first entity or a computing device, a first set of data packets related to a status query associated with the one or more health attributes of the first entity; computing, at one or more processors of the centralized server, a status information, in response to the status query based on the one or more health attributes of the first entity stored in a database of the centralized server, wherein the one or more health attributes is updated in the database using one or more inputs from any one of an external database or the first entity electronic device; and transmitting, by the one or more processors of the centralized server, to the first entity electronic device or the computing device, a second set of data packets related to the status information, in response to the status query, wherein the obtained status information is transmitted from the first entity electronic device or the computing device, using a communication interface, to the wearable electronic device, the obtained status information associated with the one or more health attributes of the first entity, to actuate an indicator of the wearable electronic device, to provide one or more unique alerts of the one or more health attributes of the first entity to the one or more proximate entities, wherein the one or more unique alerts indicate a status of the one of more health attributes to facilitate the safe physical distancing between the first entity and the one or more proximate entities for limiting pathogenic exposure therebetween.

These and other aspects of the embodiments herein will be better appreciated and understood when considered in conjunction with the following description and the accompanying drawings. It should be understood, however, that the following descriptions, while indicating exemplary embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

In the figures, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label. The embodiments herein will be better understood from the following detailed description with reference to the drawings, in which.

DETAILED DESCRIPTION

Figure 1:
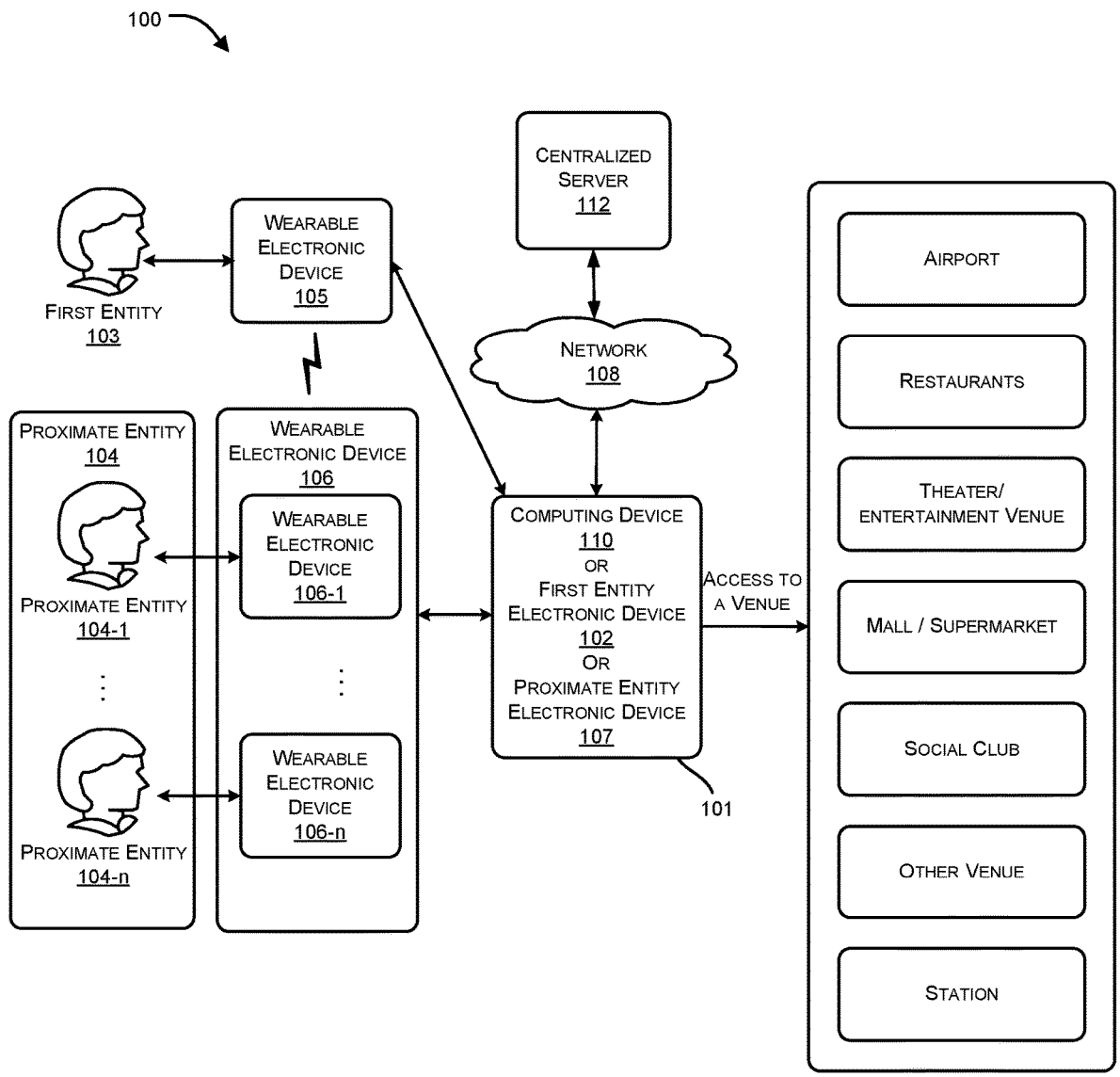
FIG. 1 illustrates an exemplary system for managing safe physical distancing between a first entity and one or more proximate entities, which may be implemented according to an embodiment herein.

The embodiments herein and the various features and advantageous details thereof are explained more fully with reference to the non-limiting embodiments that are illustrated in the accompanying drawings and detailed in the following description. Descriptions of well-known components are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide a technique to facilitate controlled access to facilities and services with intent to track exposure, limit access to and manage interactions to facilitate safe physical distancing between entities for limiting pathogenic exposure therebetween. Referring now to the drawings, and more particularly to FIGS. 1 through 10, where similar reference characters denote corresponding features consistently throughout the figures, there are shown preferred embodiments. In the drawings, the size and relative sizes of components, layers, and regions, etc. may be exaggerated for clarity.

The various modules and corresponding components described herein and/or illustrated in the figures may be embodied as hardware-enabled modules and may be a plurality of overlapping or independent electronic circuits, devices, and discrete elements packaged onto a circuit board to provide data and signal processing functionality within a computer. An example might be a comparator, inverter, or flip-flop, which could include a plurality of transistors and other supporting devices and circuit elements. The modules that include electronic circuits process computer logic instructions capable of providing digital and/or analog signals for performing various functions as described herein. The various functions can further be embodied and physically saved as any of data structures, data paths, data objects, data object models, object files, database components. For example, the data objects could include a digital packet of structured data. Example data structures may include any of an array, tuple, map, union, variant, set, graph, tree, node, and an object, which may be stored and retrieved by computer memory and may be managed by processors, compilers, and other computer hardware components. The data paths can be part of a computer CPU or GPU that performs operations and calculations as instructed by the computer logic instructions. The data paths could include digital electronic circuits, multipliers, registers, and buses capable of performing data processing operations and arithmetic operations (e.g., Add, Subtract, etc.), bitwise logical operations (AND, OR, XOR, etc.), bit shift operations (e.g., arithmetic, logical, rotate, etc.), complex operations (e.g., using single clock calculations, sequential calculations, iterative calculations, etc.). The data objects may be physical locations in computer memory and can be a variable, a data structure, or a function. Some examples of the modules include relational databases (e.g., such as Oracle® relational databases), and the data objects can be a table or column, for example. Other examples include specialized objects, distributed objects, object-oriented programming objects, and semantic web objects. The data object models can be an application programming interface for creating HyperText Markup Language (HTML) and Extensible Markup Language (XML) electronic documents. The models can be any of a tree, graph, container, list, map, queue, set, stack, and variations thereof, according to some examples. The data object files can be created by compilers and assemblers and contain generated binary code and data for a source file. The database components can include any of tables, indexes, views, stored procedures, and triggers.

In other examples, the modules described herein may be programmable modules and may be configured as a computer program product that includes a pre-configured set of instructions, which when performed, can result in actions as stated in conjunction with the methods and techniques described herein. In an example, the pre-configured set of instructions may be stored on a tangible non-transitory computer readable medium or a program storage device. In an example, the tangible non-transitory computer readable medium may be configured to include the set of instructions, which when performed by a device, can cause the device to perform acts similar to the ones described here. Embodiments herein may also include tangible and/or non-transitory computer-readable storage media for carrying or having computer executable instructions or data structures stored thereon.

Generally, program modules include routines, programs, components, data structures, objects, and the functions inherent in the design of special-purpose processors, etc. that perform particular tasks or implement particular abstract data types. Computer executable instructions, associated data structures, and program modules represent examples of the program code means for executing steps of the methods disclosed herein. The particular sequence of such executable instructions or associated data structures represents examples of corresponding acts for implementing the functions described in such steps. The embodiments herein can include both hardware and software elements. The embodiments that are implemented in software include but are not limited to, firmware, resident software, microcode, etc.

Various methods described herein may be practiced by combining one or more machine-readable storage media containing the code according to the present invention with appropriate standard computer hardware to execute the code contained therein. An apparatus for practicing various embodiments herein may involve one or more computers (or one or more processors within a single computer) and storage systems containing or having network access to computer program(s) coded in accordance with various methods described herein, and the method steps of the invention could be accomplished by modules, routines, subroutines, or subparts of a computer program product.

If the specification states a component or feature "may", "can", "could", or "might" be included or have a characteristic, that particular component or feature is not required to be included or have the characteristic.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Exemplary embodiments will now be described more fully hereinafter with reference to the accompanying drawings, in which exemplary embodiments are shown. These exemplary embodiments are provided only for illustrative purposes and so that embodiments herein will be thorough and complete and will fully convey the scope of the embodiments herein to those of ordinary skill in the art. The embodiments herein disclosed may, however, be embodied in many different forms and should not be construed as limited to the embodiments set forth herein. Various modifications will be readily apparent to persons skilled in the art. The general principles defined herein may be applied to other embodiments and applications without departing from the spirit and scope of the embodiments herein. Moreover, all statements herein reciting embodiments of the embodiments herein, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Also, the terminology and phraseology used is for the purpose of describing exemplary embodiments and should not be considered limiting. Thus, the embodiments herein are to be accorded the widest scope encompassing numerous alternatives, modifications, and equivalents consistent with the principles and features disclosed. For the purpose of clarity, details relating to technical material that is known in the technical fields related to the embodiments herein have not been described in detail so as to not unnecessarily obscure the embodiments herein.

Thus, for example, it will be appreciated by those of ordinary skill in the art that the diagrams, schematics, illustrations, and the like represent conceptual views or processes illustrating systems and methods embodying the embodiments herein. The functions of the various elements shown in the figures may be provided through the use of dedicated hardware as well as hardware capable of executing associated software. Similarly, any switches shown in the figures are conceptual only. Their function may be carried out through the operation of program logic, through dedicated logic, through the interaction of program control and dedicated logic, or even manually, the particular technique being selectable by the entity implementing the embodiments herein. Those of ordinary skill in the art further understand that the exemplary hardware, software, processes, methods, and/or operating systems described herein are for illustrative purposes and, thus, are not intended to be limited to any particular named element.

The embodiments herein may be provided as a computer program product, which may include a machine-readable storage medium tangibly embodying thereon instructions, which may be used to program the computer (or other electronic devices) to perform a process. The term "machine-readable storage medium" or "computer-readable storage medium" includes, but is not limited to, fixed (hard) drives, magnetic tape, floppy diskettes, optical disks, compact disc read-only memories (CD-ROMs), and magneto-optical disks, semiconductor memories, such as ROMs, PROMs, random access memories (RAMs), programmable read-only memories (PROMs), erasable PROMs (EPROMs), electrically erasable PROMs (EEPROMs), flash memory, magnetic or optical cards, or other type of media/machine-readable medium suitable for storing electronic instructions (e.g., computer programming code, such as software or firmware). A machine-readable medium may include a non-transitory medium in which data may be stored and that does not include carrier waves and/or transitory electronic signals propagating wirelessly or over wired connections. Examples of a non-transitory medium may include but are not limited to, a magnetic disk or tape, optical storage media such as compact disk (CD) or digital versatile disk (DVD), flash memory, memory or memory devices. A computer program product may include code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, the embodiments herein may be implemented by hardware, software, firmware, middleware, microcode, hardware description languages, or any combination thereof. When implemented in software, firmware, middleware or microcode, the program code or code segments to perform the necessary tasks (e.g., a computer-program product) may be stored in a machine-readable medium. A processor(s) may perform the necessary tasks.

Systems depicted in some of the figures may be provided in various configurations. In some embodiments, the systems may be configured as a distributed system where one or more components of the system are distributed across one or more networks in a cloud computing system.

All methods described herein may be performed in any suitable order unless otherwise indicated herein or otherwise clearly contradicted by context. The use of any and embodiments herein is intended merely to better illuminate the embodiments herein and does not pose a limitation on the scope of the embodiments herein otherwise claimed. No language in the specification should be construed as indicating any non-claimed element essential to the practice of the embodiments herein.

Various terms as used herein are shown below. To the extent a term used in a claim is not defined below, it should be given the broadest definition persons in the pertinent art have given that term as reflected in printed publications and issued patents at the time of filing.

The term "pathogenic exposure" refers to a risk of exposure to a pathogen posed to uninfected entities from a pathogen infected entity either by direct contact or action such as sneezing, coughing, and the like, or through contact of any surface touched by the infected entity.

The term "safe physical distancing" refers to maintaining of a minimum physical distance between a possibly infected entity and an uninfected entity that may limit pathogenic exposure.

FIG. 1 illustrates generally but not by the way of limitation, among other things, an exemplary system 100 including a computerized centralized server 112 for managing safe physical distancing between a first entity and one or more proximate entities, which may be implemented according to an embodiment herein. As illustrated in FIG. 1, a wearable electronic device 105 may be worn by or attached to a first entity 103, wherein the first entity 103 may be at a physical distance from one or more proximate entities (104-1, 104-2, . . . 104-*n*), collectively referred hereinafter as 104. The wearable electronic device 105 of the first entity 103 may communicate with a first entity electronic device 102 associated with the first entity 103, using any suitable communication interface such as wired or wireless communication. The proximate entities 104 may wear other wearable electronic devices (106-1, 106-2, . . . 106-*n*), collectively referred hereinafter as 106, which may communicate with their respective proximate entity electronic devices (shown collectively as 107), using the communication interface. The wearable electronic device 105 and the other wearable electronic devices 106 may communicate with each other and/or with a computing device 110, using the communication interface. The first entity electronic device 102, proximate entity electronic devices 107, and/or the computing device 110 (collectively referred to as 101) may communicate with a centralized server 112 through a network 108. The first entity 103 and proximate entity 104 may be a human or animal.

An embodiment herein provides a wearable electronic device 105 (or 106) worn by the first entity 103 (or the proximate entities 104) to indicate one or more health attributes of the first entity 103 (or the proximate entities 104) to facilitate safe physical distancing between the first entity 103 and the one or more proximate entities 104 for limiting pathogenic exposure. In an embodiment, the wearable electronic device 105 (or 106) may be attached to the first entity 103 (or the proximate entities 104) in the form of a band including, but is not limited to, a wristband, armband, waistband, and ankle band. In accordance with another embodiment herein, the wearable electronic device 105 (or 106) may be attached to the first entity 103 (or the proximate entities 104) in the form of a patch that may be fixated on any portion of the body as per convenience or requirements. In accordance with another embodiment herein, the wearable electronic device 105 (or 106) may be configured as an accessory of daily usage, or integrated with daily used accessories including, but is not limited to, a wristwatch, an ear pod, and jewelry, including a ring, bracelet, necklace, anklet, or other suitable item of jewelry. Various embodiments may be realized with respect to aesthetics, mode of attachment or the wearability of the wearable electronic device 105 (or 106), wherein, irrespective of the aesthetics, mode of attachment or the wearability, the wearable electronic device 105 (or 106) may have one or components as indicated in the following embodiments.

The wearable electronic device 105 (or 106) may include a housing 312 (shown in FIG. 3C) to attach to the first entity 103 (or the proximate entities 104). In an embodiment, the housing 312 may include one or more fastening members to provide a flexible and adjustable attachment to body of the first entity 103 (or the proximate entities 104). In an embodiment, the wearable electronic device 105 (or 106) can include one or more electrical components within the housing 312. In an embodiment, the wearable electronic device 105 (or 106) may include one or more sensors 316 (shown in FIG. 3C) disposed in the housing 312, wherein the sensors 316 may sense one or more health attributes of the first entity 103 (or the proximate entities 104). The wearable electronic device 105 (or 106) may include a transceiver 354 (shown in FIG. 3C) associated with an identifier tag 356 (shown in FIG. 3C), wherein the transceiver 354 may enable communication of the one or more sensors 316 with at least one of a first entity electronic device 102 (or proximate entity electronic device 107) and the computing device 110. In an exemplary embodiment, the identifier tag 356 may include any of a radio frequency identification (RFID) tag and Bluetooth® Low Energy (BLE) identifier. In an exemplary embodiment, the transceiver 354 may include a Bluetooth® Low Energy (BLE) transceiver. In an embodiment, the wearable electronic device 105 (or 106) may include an indicator 310 (shown in FIG. 3C) integrated with the housing 312 to facilitate the safe physical distancing between the first entity 103 and the one or more proximate entities 104 for limiting pathogenic exposure therebetween by providing one or more unique alerts of the one or more health attributes of the first entity 103 to the one or more proximate entities 104, wherein the one or more unique alerts indicate a status of the one of more health attributes.

In an embodiment, the one or more sensors 316 that enable to sense one or more health attributes of the first entity 103 (or proximate entities 104) may include any of a pedometer, an accelerometer, a light sensor, an optical sensor, an infrared sensor, and a temperature sensor. The sensors 316 may sense an activity of the first entity 103 (or proximate entities 104) or presence of a condition selected from fever, cough, shortness of breath, tiredness, body ache, muscle ache, headache, nausea, sore throat, and runny nose, among other health conditions.

In an embodiment, the indicator 310 may include at least one of a visual indicator, a light indicator, a haptic indicator, and a sound indicator. The indicator 310 may provide one or more unique alerts that may indicate status of the one of more health attributes associated with the first entity 103 (or proximate entities 104). In an exemplary embodiment, the indicator 310 may include a light emitting diode (LED) indicator, which may be disposed within the housing 312 of the wearable electronic device 105 (or 106). The indicator 310 may be associated with one or more illumination zones on the housing 312, to visually display one or more unique alerts. In an embodiment, each illumination zone may be associated with the one or more health attributes of the first entity 103 (or proximate entities 104), and each zone may visually display a different color as the unique alert depending on the status of the one of more health attributes of the first entity 103 (or proximate entities 104). As an example, one of the illumination zones may be associated with the health attribute concerning possibility of viral and/or bacterial infection of the first entity 103, wherein the illumination zone may display a red color, for example, as the unique alert that may indicate first entity 103 being viral infection positive, whereas for a viral infection negative status, the illumination zone may display a green color, for example. The various embodiments related to the working of the illumination zones on the indicator 310 and the various indicated unique alerts may be further clear from the embodiments covering system and method of the present disclosure. The color choices for display may include any suitable color(s), and accordingly the embodiments herein are not restricted to a particular color or set of colors.

In an embodiment, the wearable electronic device 105 (or 106) may include a power source 314 (shown in FIG. 3C) to power one or more electrical components present in the wearable electronic device 105 (or 106). In an embodiment, the power source 314 may be any of a battery, a rechargeable battery, lithium ion battery, and a solar cell. The wearable electronic device 105 (or 106) may include a display 302 for showing status of the power source 314. Alternatively, the status of the power source 314 may be displayed on the first entity electronic device 102 (or proximate entity electronic device 107), upon communication therebetween through the communication interface.

An embodiment herein provides a system to manage safe physical distancing between a first entity 103 and one or more proximate entities 104. As illustrated in FIG. 1, the system includes the wearable electronic device 105 worn by the first entity 103, the centralized server 112 and the one or more computing devices 110. The wearable electronic device 105, 106 may include one or more sensors 316 to sense one or more health attributes of the first entity 103, the transceiver 354 to enable communication of the wearable electronic device 105 with at least one of the first entity electronic device 102 associated with the first entity 103 and the computing device 110, and the indicator 310 coupled to the one or more sensors 316 and the transceiver 354, to provide one or more unique alerts of the one or more health attributes of the first entity 103 to the one or more proximate entities 104, wherein the one or more unique alerts indicate a status of the one of more health attributes. In an embodiment, the communication interface may include the transceiver 354 on the wearable electronic device 105, and the identity attribute may include a Bluetooth® Low Energy (BLE) identifier associated with the transceiver 354.

Figure 2A:
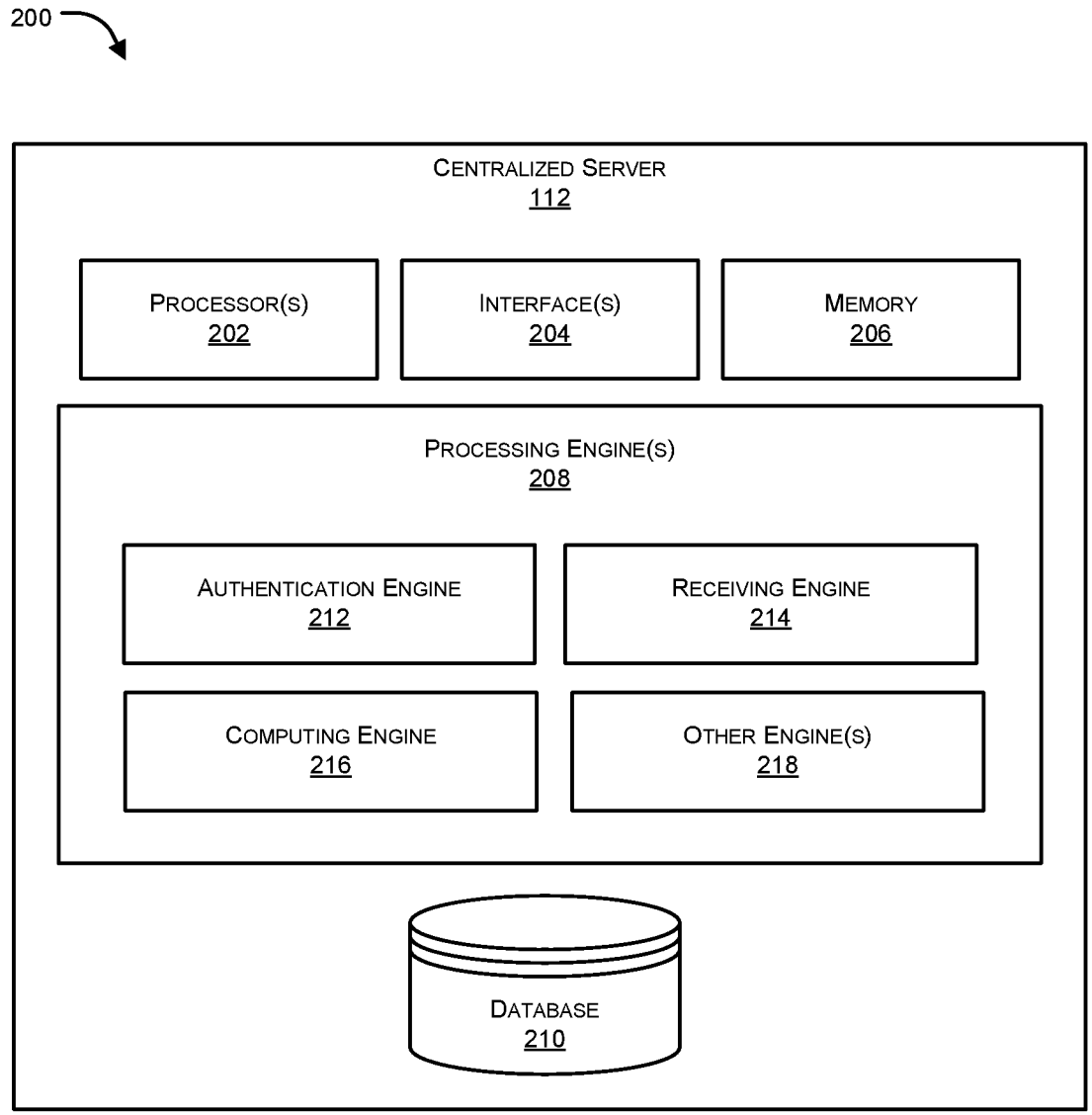
FIG. 2A illustrates an exemplary system for the centralized server of FIG. 1, according to an embodiment herein.

FIG. 2A, with reference to FIG. 1, illustrates an exemplary system 200 for the centralized server 112 of FIG. 1, according to an embodiment herein. The centralized server 112 may include one or more processors 202 coupled with a memory 206, the memory 206 storing instructions which when executed by the one or more processor(s) 202 cause the system to receive, from the first entity electronic device 102 or the computing device 110, a first set of data packets related to a status query associated with the one or more health attributes of the first entity 103; compute a status information, in response to the status query based on the one or more health attributes stored in a database 210 of the centralized server 112, wherein the one or more health attributes may be updated in the database 210 using one or more inputs from any one of an external database and the first entity electronic device 102, wherein the first entity electronic device 102 may provide the inputs to the database based on a manual entry by the first entity 103 or automatically through the one or more sensors 316 of the wearable electronic device 105; and transmit to the first entity electronic device 102 or the computing device 110, a second set of data packets related to the status information, in response to the status query. The one or more computing devices 110 may be communicably coupled to the centralized server 112, and may transmit, using the communication interface, to the wearable electronic device 105, the obtained status information from the centralized server 112, to actuate an indicator 310 of the wearable electronic device 105, to provide one or more unique alerts to manage the safe physical distancing between the first entity 103 and the one or more proximate entities 104 for limiting pathogenic exposure therebetween. In an embodiment, the external database may be a database of any of a national health agency, a hospital, a clinic, a testing center and a medical center.

The processor(s) 202 may be implemented as one or more microprocessors, microcomputers, microcontrollers, digital signal processors, central processing units, logic circuitries, and/or any devices that process data based on operational instructions. Among other capabilities, the one or more processor(s) 202 may be configured to fetch and execute computer-readable instructions stored in a memory 206 of the centralized server 112. The memory 206 may be configured to store one or more computer-readable instructions or routines in a non-transitory computer readable storage medium, which may be fetched and executed to create or share data packets over a network service. The memory 206 may comprise any non-transitory storage device including, for example, volatile memory such as RAM, or non-volatile memory such as EPROM, flash memory, and the like.

According to an embodiment herein, the centralized server 112 may include an interface(s) 204. The interface(s) 204 may comprise a variety of interfaces, for example, interfaces for data input and output devices, referred to as I/O devices, storage devices, and the like. The interface(s) 204 may facilitate communication of the centralized server 112. The interface(s) 204 may also provide a communication pathway for one or more components of the centralized server 112. Examples of such components include, but are not limited to, processing engine(s) 208 and the database 210.

The processing engine(s) 208 may be implemented as a combination of hardware and programming (for example, programmable instructions) to implement one or more functionalities of the processing engine(s) 208. In examples described herein, such combinations of hardware and programming may be implemented in several different ways. For example, the programming for the processing engine(s) 208 may be processor executable instructions stored on a non-transitory machine-readable storage medium and the hardware for the processing engine(s) 208 may comprise a processing resource (for example, one or more processors), to execute such instructions. In the present examples, the machine-readable storage medium may store instructions that, when executed by the processing resource, implement the processing engine(s) 208. In such examples, the centralized server 112 may comprise the machine-readable storage medium storing the instructions and the processing resource to execute the instructions, or the machine-readable storage medium may be separate but accessible to the centralized server 112 and the processing resource. In other examples, the processing engine(s) 208 may be implemented by electronic circuitry. The processing engine(s) 208 may include one or more engines selected from any of an authentication engine 212, a receiving engine 214, a computing engine 216 and other engine(s) 218 for processing one or more instructions. In an embodiment, the authentication engine may authenticate the first entity electronic device 102 or the computing device 110 to access the database 210, based on one or more authenticating criteria set. The authenticating criteria may either only include access to the identity attribute of the transceiver 354 (e.g., BLE transceiver) on the wearable electronic device 105 of the first entity 103, or may be combined with other criterion such as first entity identity details, phone number and the like, such that upon getting successful authentication, the authenticating engine 212 may allow accepting any status query. In an embodiment, the receiving engine 214 may enable receiving one or more status queries from the first entity electronic device 102 (or proximate entity electronic device 107). In an embodiment, the computing engine 216 may compute the status information, in response to the status query based on the one or more health attributes of the first entity 103 stored in the database 210 of the centralized server 112. The other engine(s) 218 may enable to update the database 210 based on inputs received from an external database or the first entity electronic device 102 (or proximate entity electronic device 107), which may in turn may receive the inputs from the wearable electronic device 105 (or 106).

The database 210 may comprise data that may be either stored or generated as a result of functionalities implemented by any of the components of the processing engine(s) 208 or the centralized server 112. In an embodiment, the database 210 may be linked to an external database of any of a national health agency, a hospital, a clinic, a testing center and a medical center, to collect information related to health of the entities (103 or 104), which may be private or public information, wherein the private information may be accessed by the centralized server 112, by consent from the respective entities (103 or 104).

In an embodiment, the computing device 110 may be present at any venue that may implement the system of the present disclosure to manage safe physical distancing between the first entity 103 and one or more proximate entities 104. The computing device 110 may be communicably coupled to the centralized server 112, for transmitting the status query to the centralized server 112, and may further transmit the obtained status information from the centralized server 112 to the wearable electronic device (105 or 106), using a communication interface to actuate the indicator 310 of the wearable electronic device (105 or 106), to provide the one or more unique alerts to manage the safe physical distancing between the first entity 103 and the one or more proximate entities 104 for limiting pathogenic exposure therebetween. In an embodiment, the computing device 110 at the venue, may obtain authentication before it may transmit the status query to the centralized server 112, wherein the authentication may be based on the identity attribute of the wearable electronic device 105 (or 106). In another embodiment, a two-step authentication criterion may be set, which may require the identity attribute of the wearable electronic device 105 (or 106) as well as providing any of entity identity details, a phone number, one time password, social media handle, and email address, etc. of the entity.

In an embodiment, and as illustrated in FIG. 1, the venue may be any of an airport, a restaurant, a theater, an entertainment venue, a mall, a supermarket, a social club, a station, and other public, government, or private venues. The device, system, and the method provided by the embodiments herein may be implemented to manage safe physical distancing between different people or entities at the mentioned venues or any other venues involving large crowds or places of public gathering, especially in pandemic or other high risk situations, wherein it may be necessary to manage and/or restrict access to a venue based on the health status of the entities and to manage safe physical distancing after such access may be allowed.

In an implementation, the first entity electronic device 102 (or proximate entity electronic device 107) may be accessed by applications residing on any operating system, including but is not limited to, Android®, iOS™, and the like. In an embodiment, the first entity electronic device 102 may include, but is not limited to, any of a smartphone, a mobile electronic device, and a smart computing device. The term "a smart computing device" refers to any computing device that may be connected to other devices or networks via various wireless protocols, and may operate interactively or independently. In an embodiment, the first entity electronic device 102 may be a mobile phone(s) associated with input device(s). The first entity electronic device 102 is not be restricted to the above-mentioned devices and various other devices may be used.

In an embodiment, the first entity electronic device 102 (or proximate entity electronic device 107) may include a touch pad, touch enabled screen, an integrated sensing unit, an image scanner, and the like. In an embodiment, the first entity electronic device 102 may include a mobile application that may be used to regularly access the health status, update the health attributes or to access other functionalities that may be discussed in various embodiments herein. The communication interface may be selected from, but is not limited to, any of a Bluetooth® Low Energy (BLE), radio frequency (RF) and near field communication (NFC).

The embodiments herein may provide a computer program product configured to include a pre-configured set of instructions, which when performed, may result in one or more actions. An embodiment herein provides a non-transitory computer readable storage medium storing the pre-configured set of instructions or one or more sequences of instructions, which when executed by one or more processors, causes indicating one or more health attributes of the first entity 103 on a wearable electronic device 105 to facilitate safe physical distancing between the first entity 103 and one or more proximate entities 104 for limiting pathogenic exposure, by performing a method that may include receiving, at the centralized server 112, from a first entity electronic device 102 associated with the first entity 103 or a computing device 110, a first set of data packets related to a status query associated with the one or more health attributes of the first entity 103; computing, at one or more processors of the centralized server 112, a status information, in response to the status query based on the one or more health attributes of the first entity 103 stored in a database 210 of the centralized server 112, wherein the one or more health attributes may be updated in the database 210 using one or more inputs from any one of an external database or the first entity electronic device 102; and transmitting, by the one or more processors of the centralized server 112, to the first entity electronic device 102 or the computing device 110, a second set of data packets related to the status information, in response to the status query. The obtained status information may be transmitted from the first entity electronic device 102 or the computing device 110, using a communication interface, to the wearable electronic device 105, the obtained status information associated with the one or more health attributes of the first entity 103, to actuate the indicator 310 of the wearable electronic device 105, to provide one or more unique alerts of the one or more health attributes of the first entity 103 to the one or more proximate entities 104, wherein the one or more unique alerts indicate a status of the one of more health attributes to facilitate the safe physical distancing between the first entity 103 and the one or more proximate entities 104 for limiting pathogenic exposure therebetween.

In an example, the pre-configured set of instructions may be stored on a tangible non-transitory computer readable medium. In an example, the tangible non-transitory computer readable medium may be configured to include the set of instructions, which when performed by the computing device, may cause the computing device to perform acts similar to the ones described. Computer-executable instructions, associated data structures, and program modules represent examples of the program code means for executing steps disclosed herein. The particular sequence of such executable instructions or associated data structures represents examples of corresponding acts for implementing the functions described in such steps.

The techniques provided by the embodiments herein may be implemented on an integrated circuit chip. The chip design is created in a graphical computer programming language and stored in a computer storage medium (such as a disk, tape, physical hard drive, or virtual hard drive such as in a storage access network). Chips or photolithographic masks used to produce chips, may be fabricated, or the resulting design may be transmitted by physical means (e.g., by providing a copy of the storage medium storing the design) or electronically (e.g., through the Internet), directly or indirectly. The stored design may be then converted into the appropriate format (e.g., GDSII) for the fabrication of photolithographic masks, which typically include multiple copies of the chip design in question that are to be formed on a wafer. The photolithographic masks may be utilized to define areas of the wafer (and/or the layers thereon) to be etched or otherwise processed.

The resulting integrated circuit chip may be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product may be any product that includes integrated circuit chips, ranging from toys and other low-end applications to advanced computer products having a display, a keyboard or other input device, and a central processor. A data processing system suitable for storing and/or executing program code may include at least one processor coupled directly or indirectly to memory elements through a system bus. The memory elements may include local memory employed during actual execution of the program code, bulk storage, and cache memories which provide temporary storage of at least some program code in order to reduce the number of times code must be retrieved from bulk storage during execution. Input/output (I/O) devices (including but is not limited to keyboards, displays, pointing devices, etc.) may be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

Figure 2B:
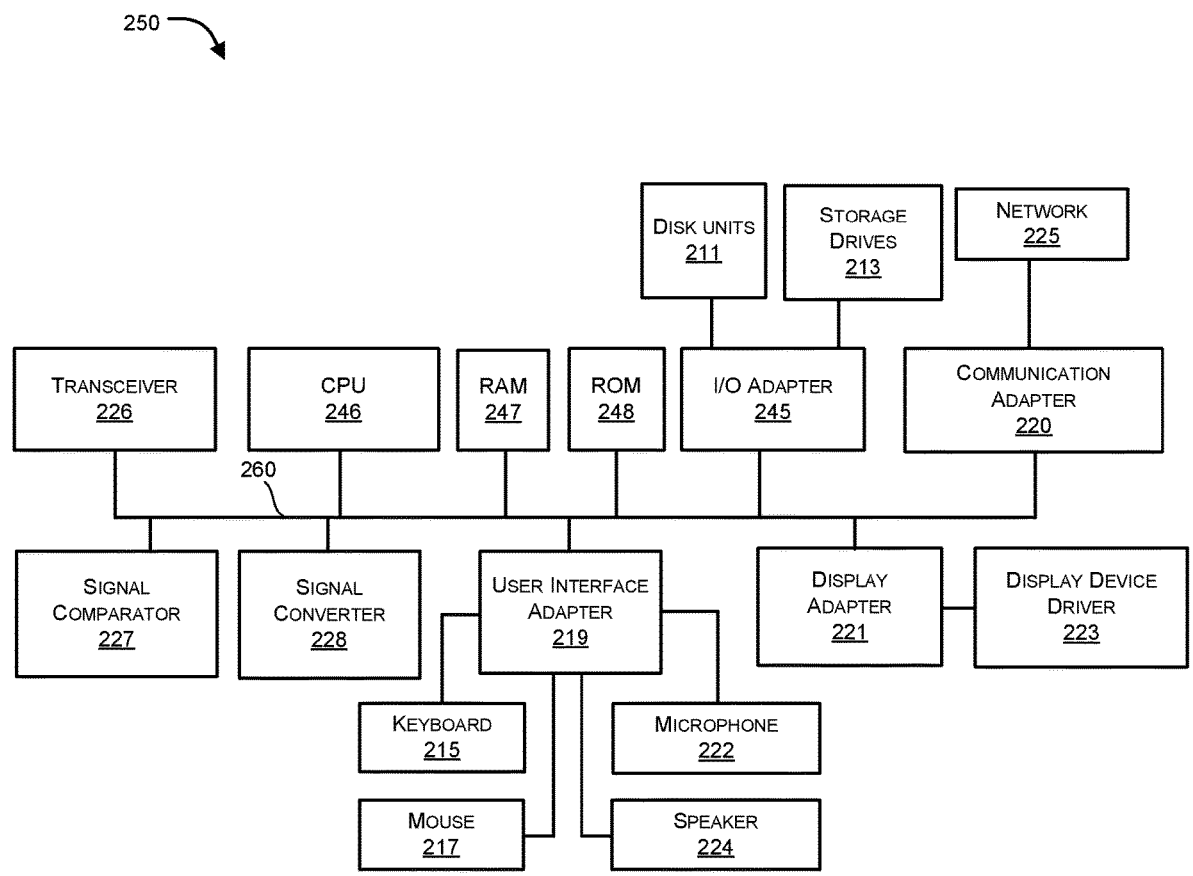
FIG. 2B illustrates an exemplary computer system, according to an embodiment herein.

A representative hardware environment for practicing the embodiments herein is depicted in FIG. 2B, with reference to FIGS. 1 and 2A. This schematic drawing illustrates a hardware configuration of an information handling/computer system 250 in accordance with an exemplary embodiment herein. The system 250 comprises at least one processor or central controller (CPU) 246. Examples of CPU 246 include, but are not limited to, an Intel® Itanium® or Itanium 2™ processor(s), or AMD® Opteron® or Athlon MP® processor(s), Motorola® lines of processors, FortiSOC™ system on chip processors or other future processors. The CPU 246 may include various modules associated with embodiments herein. The CPUs 246 may be interconnected via system bus 260 to various devices such as a random access memory (RAM) 247, read-only memory (ROM) 248, and an input/output (I/O) adapter 245. The read-only memory 248 can be any static storage device(s) e.g., but is not limited to, a Programmable Read Only Memory (PROM) chips for storing static information e.g., start-up or BIOS instructions for CPU 246. Mass storage may be any current or future mass storage solution, which can be used to store information and/or instructions. Exemplary mass storage solutions include, but are not limited to, Parallel Advanced Technology Attachment (PATA) or Serial Advanced Technology Attachment (SATA) hard disk drives or solid-state drives (internal or external, e.g., having Universal Serial Bus (USB) and/or Firewire interfaces), e.g. those available from Seagate® (e.g., the Seagate Barracuda 7102 family) or Hitachi® (e.g., the Hitachi Deskstar 7K1000), one or more optical discs, Redundant Array of Independent Disks (RAID) storage, e.g. an array of disks (e.g., SATA arrays), available from various vendors including Dot Hill Systems Corp., LaCie, Nexsan Technologies, Inc. and Enhance Technology, Inc.

The I/O adapter 245 may connect to peripheral devices, such as disk units 211 and storage drives 213, or other program storage devices that are readable by the system 250. The system 250 may read the computer-executable instructions on the program storage devices and follow these instructions to execute instructions. The system 250 may further include a user interface adapter 219 that connects a keyboard 215, mouse 217, speaker 224, microphone 222, and/or other user interface devices such as a touch screen device (not shown) to the bus 260 to gather user input. Additionally, a communication adapter 220 connects the bus 260 to a data processing network 225, and a display adapter 221 connects the bus 260 to a display device driver 223, which provides a GUI (e.g., a gadget) in accordance with the embodiments herein, or which may be embodied as an output device such as a display device, monitor, printer, or transmitter, for example. Further, a transceiver 226, a signal comparator 227, and a signal converter 228 may be connected to the bus 260 for processing, transmission, receipt, comparison, and conversion of electric or electronic signals. The bus 260 communicatively couples CPU 246 with the other memory, storage and communication blocks. The bus 420 can be, e.g. a Peripheral Component Interconnect (PCI)/PCI Extended (PCI-X) bus, Small Computer System Interface (SCSI), USB or the like, for connecting expansion cards, drives and other subsystems as well as other buses, such a front side bus (FSB), which connects CPU 246 to software system.

Figure 3A:
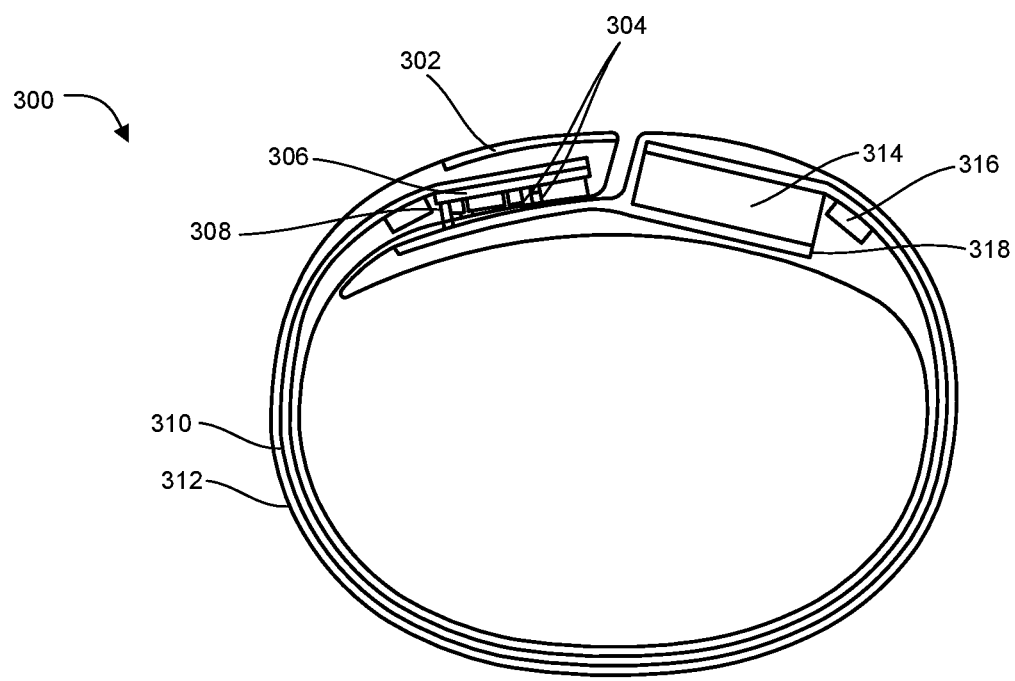
FIG. 3A illustrates an exemplary representation depicting a side view of a wearable electronic device, according to an embodiment herein.
Figure 3B:
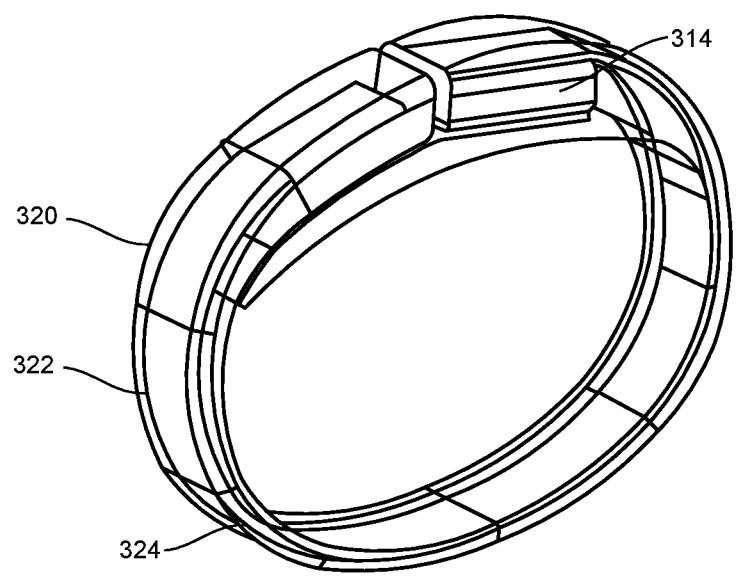
FIG. 3B illustrates an exemplary representation depicting an isometric view of a wearable electronic device, according to an embodiment herein.
Figure 3C:
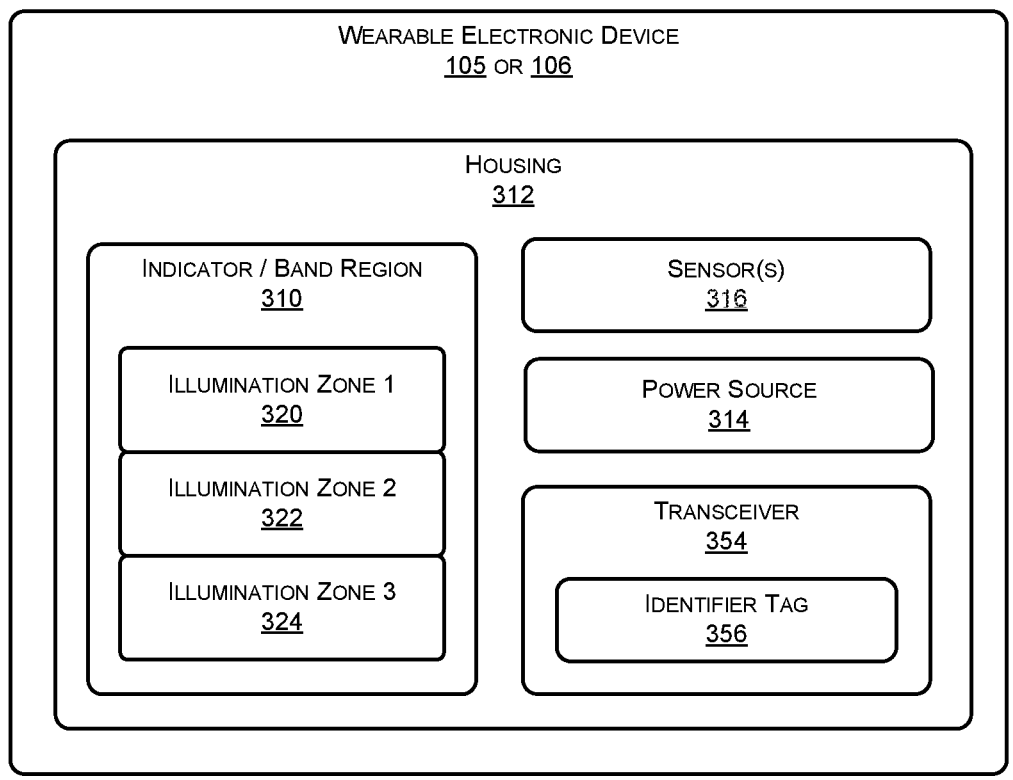
FIG. 3C illustrates a block diagram for an exemplary representation of a wearable electronic device, according to an embodiment herein.

FIGS. 3A through 3C, with reference to FIGS. 1 through 2B, illustrate an exemplary wearable electronic device 300 which may be an exemplary representation of the wearable electronic device 105 (or 106), in accordance with an embodiment herein, wherein FIG. 3A illustrates a side view of the exemplary wearable electronic device 300, FIG. 3B illustrates an isometric view of the exemplary wearable electronic device 300, and FIG. 3C illustrates a block diagram for an exemplary representation of the wearable electronic device 105 (or 106). As per the embodiment herein, the wearable electronic device 300 may be a wristband, which may be worn around wrist of the first entity 103 (or proximate entities 104). The wearable electronic device 300 may include a housing 312 to attach to the first entity 103. The housing 312 may be plastic, rubber, metal, or any combination thereof. The housing 312 can include a buckle, magnets, clips or any other suitable retaining mechanism(s) to open/close the housing 312 for suitable attachment/detachment to/from the first entity 103. The wearable electronic device 300 may include one or more sensors 316 disposed in the housing 312 to sense the one or more health attributes of the first entity 103. The wearable electronic device 300 may include a transceiver 354 associated with an identifier tag 356, wherein the transceiver 354 may enable communication of the one or more sensors 316 with at least one of a first entity electronic device 102 associated with the first entity 103 and a computing device 110. The wearable electronic device 300 may include an indicator or a band region 310, wherein the indicator 310 may be a LED indicator integrated with the housing 312 such that the indicator or the band region 310 may be associated with one or more illumination zones (320, 322, 324), namely a first zone 320 a second zone 322 a third zone 324 on the housing 312, to visually display the one or more unique alerts, and wherein each illumination zone (320, 322, 324) may be associated with the one or more health attributes of the first entity 103, to facilitate the safe physical distancing between the first entity 103 and the one or more proximate entities 104 for limiting pathogenic exposure, wherein the one or more unique alerts indicate a status of the one of more health attributes. The wearable electronic device 300 may include a power source 314 in the form of a lithium battery to power one or more electrical components of the wearable electronic device 300. In another example, the power source 314 may comprise solar cells to receive solar energy to generate the power. The wearable electronic device 300 may include other components such as a pogo pin 308, a magnetic connector (318, 304), a printed circuit board (PCB) 306, and a display 302. The wearable electronic device 300 may not be restricted to a wristband and various other embodiments may be possible and several other electrical components may be included to add other functional aspects based on the type of the wearable electronic device 300.

Figure 4:
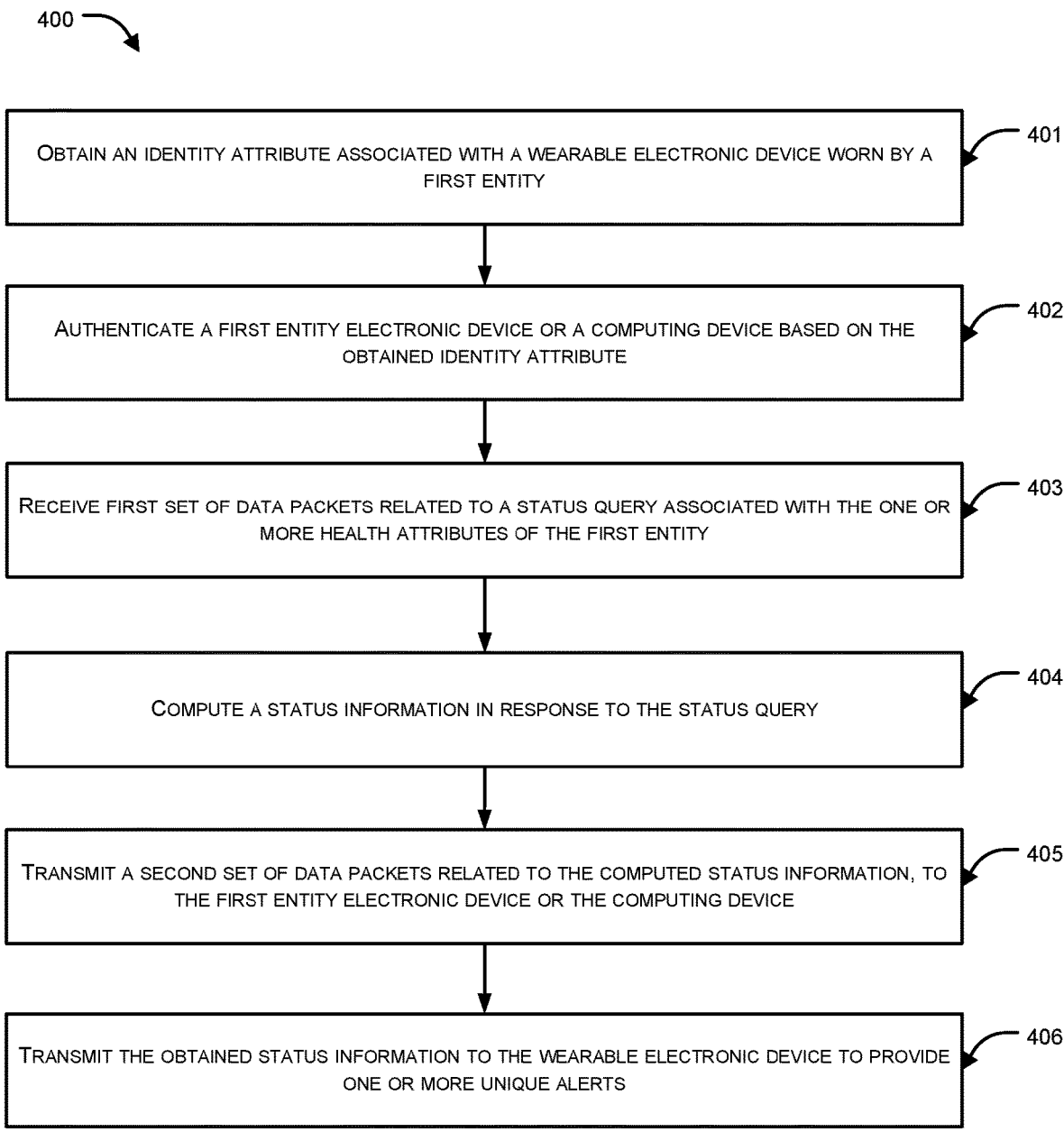
FIG. 4 illustrates a flow diagram depicting an exemplary representation of a method for indicating one or more health attributes of a first entity on a wearable electronic device, according to an embodiment herein.

FIG. 4, with reference to FIGS. 1 through 3C, illustrates a flow diagram depicting an exemplary representation of a method 400 for indicating one or more health attributes of a first entity 103 on a wearable electronic device 105 (or 106) to facilitate safe physical distancing between the first entity 103 and one or more proximate entities 104 for limiting pathogenic exposure, according to an embodiment herein. With reference to FIG. 4, an embodiment herein, provides a method including the following. At 401, the method 400 includes the step of obtaining, using a computing device 110 or a first entity electronic device 102 associated with the first entity 103, an identity attribute associated with a wearable electronic device 105 worn by the first entity 103. At 402, the method 400 includes authenticating, based on the obtained identity attribute, the first entity electronic device 102 or the computing device 110, to access a database 210 of a centralized server 112.

At 403 of FIG. 4, the method 400 includes receiving, at the centralized server 112, from the first entity electronic device 102 or the computing device 110, a first set of data packets related to a status query associated with the one or more health attributes of the first entity 103. At 404 of FIG. 4, the method 400 includes computing, at one or more processors 202 of the centralized server 112, a status information, in response to the status query based on the one or more health attributes of the first entity 103 stored in the database 210 of the centralized server 112, wherein the one or more health attributes is updated in the database 210 using one or more inputs from any one of an external database or the first entity electronic device 102, and wherein the first entity electronic device 102 provides the inputs to the database 210 of the centralized server 112 based on a manual entry in the first entity electronic device 102 by the first entity 103 or through one or more sensors 316 of the wearable electronic device 105.

At 405 of FIG. 4, the method 400 includes transmitting, by the one or more processors 202 of the centralized server 112, to the first entity electronic device 102 or the computing device 110, a second set of data packets related to the computed status information. At 406 of FIG. 4, the method 400 includes transmitting, from the first entity electronic device 102 or the computing device 110, using a communication interface, to the wearable electronic device 105, the obtained status information associated with the one or more health attributes of the first entity 103, to actuate the indicator 310 of the wearable electronic device 105, to provide one or more unique alerts of the one or more health attributes of the first entity 103 to the one or more proximate entities 104, wherein the one or more unique alerts indicate a status of the one of more health attributes to facilitate the safe physical distancing between the first entity 103 and the one or more proximate entities 104 for limiting pathogenic exposure therebetween.

The method 400 may be applicable in one or more scenarios to provide the unique alerts either to the first entity 103, the proximate entities 104 or to one or more management personnel who may allow access to a venue to any of the entities (103 or 104) based on the unique alerts. In an embodiment, the sensors 316 of the wearable electronic device 105 may be used to sense one or more health attributes of the first entity 103 including, but is not limited to, an activity of the first entity 103 or presence of a condition selected from fever, cough, shortness of breath, tiredness, body ache, muscle ache, headache, nausea, sore throat, and runny nose, which may be transmitted to the first entity electronic device 102, using communication interface selected from, but is not limited to, any of a Bluetooth® Low Energy (BLE), radio frequency (RF) and near field communication (NFC).

In an embodiment, the first entity electronic device 102 may be a mobile phone device of the first entity 103, and may include an entity account which may be accessible on a mobile application by providing necessary credentials such that, upon accessing the account, one or more health attributes related to the first entity 103 may be available, which may be linked to database 210 of the centralized server 112, and may be regularly updated. In an embodiment, the first entity 103 may be able to connect to their wearable electronic device 105 to the first entity electronic device 102, by using Bluetooth® by means of the transceiver 354 present therein to enable to update one or more health attributes of the first entity 103 on the first entity electronic device 102. The first entity electronic device 102 may obtain an identity attribute such as Bluetooth® Low Energy (BLE) identifier associated with a wearable electronic device 105, upon connecting to the wearable electronic device 105. In an embodiment, upon connection, the one or more health attributes as sensed by sensors 316 of the wearable electronic device 105 may be transmitted to the first entity electronic device 102 through the transceiver 354. The BLE identifier may be associated with the entity account and thus be used to authenticate the first entity electronic device 102 to access the database 210 of a centralized server 112, to update one or more health attributes as inputs, based on a manual entry in the first entity electronic device 102 by the first entity 103 or through the sensors 316 of the wearable electronic device 105. In another embodiment, the manual entry may be entered through one or more input devices on the first entity electronic device 102, and may include any of written text, visual recording, audio recording and any information recorded by any integrated sensing unit in the first entity electronic device 102.

In an embodiment, the first entity 103 may require access to a venue which may be enabled by assessment of the one or more health attributes of the first entity 103, provided as unique alerts provided on the wearable electronic device 105. The venue may have computing device 110, which may be used to manage access or safe distancing of the entities. In an embodiment, the identity attribute associated with wearable electronic device 105 of the first entity 103 may be obtained by the computing device 110 in one or more ways. In one exemplary embodiment, the wearable electronic device 105 may contain an RFID tag for the purpose of getting identified at the venue, wherein the RFID tag may be scanned to access a RFID code present therein, by using a scanning device at the venue, which may enable to obtain the Bluetooth® Low Energy (BLE) identifier associated with the transceiver 354 of the wearable electronic device 105. In another exemplary embodiment, the wearable electronic device 105 may be directly identified by its BLE identifier. Upon obtaining the BLE identifier, the computing device 110 may be authenticated based on the BLE identifier to access database 210 of the centralized server 112, which may be queried to get unique alerts related to the health attributes of the first entity 103, to decide allowance of access to the venue, based on the unique alerts. The centralized server 112 may receive a first set of data packets from the computing device 110, which may be related to a status query associated with the one or more health attributes of the first entity 103. The centralized server 112 may compute status information, in response to the status query based on the one or more health attributes of the first entity 103 stored in the database 210, wherein the computed status information may be transmitted to the computing device 110 as a second set of data packets. The computing device 110 may then transmit the obtained status information to the wearable electronic device 105 using the transceiver 354. In an embodiment, the wearable device 105 may include a LED indicator, and one or more unique alerts may be visually displayed on the LED indicator attached to the wearable electronic device 105 to create one or more illumination zones (320, 322, 324) on the wearable electronic device 105, and wherein each illumination zone (320, 322, 324) may be associated with the one or more health attributes of the first entity 103. Each of the illumination zones (320, 322, 324) may be represented by one or more colors, wherein each color may be the unique alert or indication for a specific health status of health attributes.

In an embodiment, a first illumination zone 320 of the one or more illumination zones may indicate a first health attribute of the one or more health attributes. The first health attribute may include direct information related to a result of testing the first entity for checking a pathogenic infection. As an example, the first health attribute may be related to testing result in case of a pandemic such as coronavirus (COVID) caused by acute respiratory syndrome coronavirus 2 (SARS-CoV-2) or any other type of viral or bacterial infection. The first entity 103 may have been tested in the past for any of COVID infection and antibody test, and the corresponding testing result may be updated in the database 210 of the centralized server 112 from an external database of any health agency or voluntarily be disclosed by the first entity 103. The antibody test may reveal the previous infection possibility of the first entity 103. The result of testing may be selected from infected and active, infected and inactive, and non-infected, and may be indicated as a different color on the first illumination zone 320 of the wearable electronic device 105, as given below in the exemplary embodiments:

Color 1: COVID Negative (COVID or COVID Antibody Test Negative)
Color 2: COVID Positive Active (COVID Test Positive)
Color 3: COVID Positive Inactive (Antibody Test Positive)

In an embodiment, a second illumination zone 322 of the one or more illumination zones may indicate a second health attribute of the one or more health attributes, wherein the second health attribute may be obtained as inputs from any of the manual entry by the first entity 103 on the first entity electronic device 102 or automatically through the one or more sensors 316 of the wearable electronic device 105. The second health attribute may be mainly based on self-diagnostics of the first entity 103, as provided by manual entry on the first entity electronic device 102 by accessing the entity account on the mobile application or may also be directly updated on the first entity electronic device 102, by automatic updating when the wearable electronic device 105 may be connected to the first entity electronic device 102. The second illumination zone 322 may indicate thus self-diagnostics general wellness of the first entity 103, based on result of input by the first entity 103. The second health attribute may be related to presence of a condition including, but is not limited to, fever, cough, shortness of breath, tiredness, body ache, muscle ache, headache, nausea, sore throat, and runny nose. The second health attribute may also indicate one or more health attributes including, but is not limited to, heart rate, blood pressure, glucose level, weight change, blood oxygen level, sensed by the sensors 316 on the wearable electronic device 105, or by using a sensing device either integrated with the first entity electronic device 102 or connected to the first entity electronic device 102 through any communication interface. The sensing device may include, but is not limited to, a thermometer, blood oximeter, heart rate monitor, blood pressure monitor, weigh scale, and glucose monitor.

In an embodiment, a third illumination zone 324 of the one or more illumination zones indicates a third health attribute of the one or more health attributes. The third health attribute may be associated with a user profile data including a risk assessment of the pathogenic exposure to the first entity 103, risk assessment of the pathogenic exposure to the one or more proximate entities 104 posed by the first entity 103, and an ability of the first entity 103 to socialize with the one or more proximate entities 104 with a minimum risk of the pathogenic exposure. The risk assessment of the pathogenic exposure to the first entity 103 may be related to the risk posed to the first entity 103 in presence of the proximate entities 104 that may be indicated as a particular color of the third illumination zone 324 on the wearable electronic devices 106 worn by the proximate entities 104. The third health attribute may be indicated as a particular color of the third illumination zone 324 on the wearable electronic device 105 worn by the first entity 103. As an example, such assessment may include, but is not limited to, presence of temperature or fever in case of the first entity 103.

In an embodiment, the user profile data may be linked to the entity account that may be accessed on the computing device 110, or the mobile application on the first entity electronic device 102. In an embodiment, the user profile data may include physical attributes and social attributes. The physical attributes may include any of age, body weight, body height, pre-existing health condition and daily routine details. The social attributes may include a record of interaction of the first entity 103 with the one or more proximate entities 104, degree of contact of the first entity 103 with the one or more proximate entities 104, distance travelled by the first entity 103 from a home location to an outside location, and/or a range of area covering maximum distance travelled over a time period around the home location.

In an embodiment, the social attributes may be computed, by the one or more processors 202 of the centralized server 112, to calculate at least one score selected from a social distancing score, a direct social score, a risk receivable score, a risk transferrable score, and a total risk factor score. The calculation of each score, as per an exemplary embodiment, may be done as given below:

Social Distancing Score (SDS):

$$SDS=(1-CSR(0)/CLR(0))\times 100$$

wherein CLR(n) represents Cumulative Long-Range Contact to $n^{th}$ degree;

CSR(n) represents Cumulative Short-Range Contact to $n^{th}$ degree;

(n) represents degree of contact, wherein n=0 means direct contact, n=1 means contacts of direct contacts, n=2 means contacts of contacts of direct contacts.

Direct Social Score (DSS):

$$DSS=CSR(0)(over 14\ days)$$

Risk Receivable Score (RRS):

RRS=CSR(1) looking back 14 days; cumulative short range contacts to $1^{st}$ degree; total of all bands user has come in contact with and total of all short range contacts of those contacts for the prior 14 days.

Risk Transferrable Score (RTS):

RGS=CSR(1) looking forward 14 days; cumulative short range contacts to $1^{st}$ degree; total of all bands user has come in contact with and total of all short range contacts of those contacts for the future 14 days after the contact.

Total Risk Factor (TRF) score:

TRF=RRS*$A$(Area of maximum distance travelled by user in prior 14 days)+RGS*$A$(Area of maximum distance travelled by user in future 14 days)

In an embodiment, the record of interaction of the first entity 103 with the one or more proximate entities 104 may be updated on the first entity wearable electronic device 105, wherein the record may include a timestamp of the interaction and the distance sensed between the wearable electronic device 105 worn by the first entity 103 and a second wearable electronic device 106 worn by the one or more proximate entities 104.

In an embodiment, socializing between entities may include defining of a closed group that may enable interaction between the members of the closed group without practicing social physical distancing between the members, but may keep a track of health attributes of the members and risk posed by change in the health attributes of the members. An embodiment herein facilitates safe physical distancing between a first group of entities comprising the first entity 103, and a second group comprising the one or more proximate entities 104, wherein the first group may include a closed group and each member of the first group uses a separate wearable electronic device 105. The first entity 103 may be allowed to interact with each member of the first group without the safe physical distancing. An embodiment herein may facilitate updating the database by tracking of the separate wearable electronic devices 105 of the first group to record number of the members in the first group interacting with the first entity 103, duration of stay of the first entity 103 in the first group without any interaction with the second group and health status information of each of the member/entity in the first group.

An embodiment herein may define an optimized socializing such that the first entity 103 may be defined by a metric to socialize with other entities, without requiring social distancing. In an exemplary embodiment, such metric may involve a metric "n" which may be number of other proximate entities that the first entity 103 can socialize with, without need for social distancing, and another metric may be "t" including number of days that the first entity 103 may have remained within a closed group without any outside contact. A closed group may be defined as a group of entities who may limit their contacts to members of the same closed group only, given each member of a closed group records daily self-diagnostics general wellness information.

In an exemplary embodiment, wherein the method described in embodiments, may be implemented to track and assess risk in a pandemic such as coronavirus (COVID), a closed group day count (DC) may be derived by following the above steps:

Closed Group Day Count (DC):

Deriving number of days elapsed since the group has remained closed, and not allowed any external members to enter, wherein the closed group day count may reduce if the below events occur:

If any group member or entity may be tested COVID positive, entire group day count lapses to 0 and entire group may enter quarantine mode.

An individual member or entity may participate in another closed group with a lower day count, wherein the closed group may eject the member or entity to maintain its day count and lower its member count. The two closed groups may not interact in this case and the ejected member may effectively become a member of the other closed group. In another scenario, the member may be accepted, and the day count of the entire group may be matched with the day count of the other closed group, effectively adding the two closed groups in a bigger group.

The above actions may continue to break a group into smaller groups preserving the day count or make bigger groups by adopting the day count of lower group. An exemplary case for the same may be defined as:

$G(n,t)$; where n is number of members and t is day count.

Group 1: n=10; t=12; Group 2: n=25; t=6

In an embodiment, U1 may be a user who may be member of G1 and participates in G2, wherein G1 and G2 can exist as below:

Group 1: n=9; t=12; Group 2: n=26; t=6

Various other embodiments may be possible for managing a closed group of entities.

The one or more unique alerts on the wearable electronic device 105 may be used for alerting the first entity or the proximate entities in a number of situations. An embodiment herein may facilitate, using the one or more unique alerts on the wearable electronic devices (105, 106, or 300), to enable alerting the first entity 103 to maintain the safe physical distancing from the one or more proximate entities 104. This may be enabled such that when a first entity 103 may breach a defined safe physical distance of the one or more proximate entities 104, the wearable electronic device 105, 106, 300 may provide unique alerts on the wearable electronic devices 105, 106, 300 to allow the entities to correct their distancing. In an example, the safe physical distance may be preset in the system to a definite value such as a six-foot distance.

Another embodiment herein may facilitate, using the one or more unique alerts on the wearable electronic devices 105, 106, 300, to enable alerting the first entity 103 (or the proximate entities 104) regarding frequency or duration of hand washing, wherein the entities may be reminded by the unique alerts at time intervals preset in their wearable electronic devices 105, 106, 300 if they may have washed hands for insufficient number of times over a period of time, or the unique alert may continue until the entities wash their hands for a definite time duration in a singular event of hand wash. Another embodiment herein may facilitate, using the one or more unique alerts on the wearable electronic devices 105, 106, 300, to enable alerting the first entity on face touching movement, which may be enabled by accelerometers, light sensors or IR sensors in the wearable electronic device 105, 106, 300.

Another embodiment herein may facilitate, using the one or more unique alerts on the wearable electronic devices 105, 106, 300, to enable alerting the first entity 103 or proximate entities 104 based on location of movement, when approaching an area of relatively higher pathogenic exposure. This information may enable the entities to enter or socialize in a particular area based on the risk of exposure depending on the number of pathogen infected entities in that area, and through integration of risk factors and maps, a social network of entities may be able to communicate and help other users to perform tasks, which the other entity may personally be at a much higher risk to perform. One example may be grocery shopping for high risk entity; however, various other embodiments may be possible related to tasks performed by entities using the map functionality disclosed herein.

In an embodiment, the wearable electronic device 105 of the first entity 103 may communicate, using the communication interface, with a third wearable electronic device 106 worn by the one of the proximate entities 104 and share the status information with each other, to visibly indicate the one or more health attributes as the unique alerts. This may ensure mental satisfaction to the entities based on the visual unique alerts about the health status of their neighboring entities.

In an embodiment, the wearable electronic device 105 of the first entity 103 may maintain a record of interaction within a specified distance between the wearable electronic device 105 of the first entity 103 and wearable electronic devices 106 of the proximate entities 104 over a definite time duration to enable contact tracing. This may be useful in a scenario wherein such a record may enable to alert or indicate to the first entity 103 to stay in a quarantine mode when a proximate entity 104 that the first entity may have interacted with previously gets tested positive for a pathogen such as COVID. In an exemplary embodiment, details of every infected proximate entity that the first entity 103 comes within short range for a period of 14 days, may be recorded for allowing contact tracing, and in an event, the infected proximate recovers or tests negative, then all short-range contacts including the first entity 103 may be notified using mobile application on the entity electronic device (102 or 107). In an embodiment, the update in the health status of the entities may be updated in the database 210, with prior permission from the entity.

In an embodiment, the wearable electronic device 105 of the first entity 103, upon encountering a third wearable electronic device 106 worn by one of the proximate entities 104, may excite the third wearable electronic device 106, using the first entity electronic device 102 or the computing device 110 at the venue, to provide the one or more unique alerts associated with one or more health attributes of the proximate entity 104. This may enable to provide clear visual cue regarding any proximate entity for greater mental satisfaction of being safe in a public place.

Figure 5:
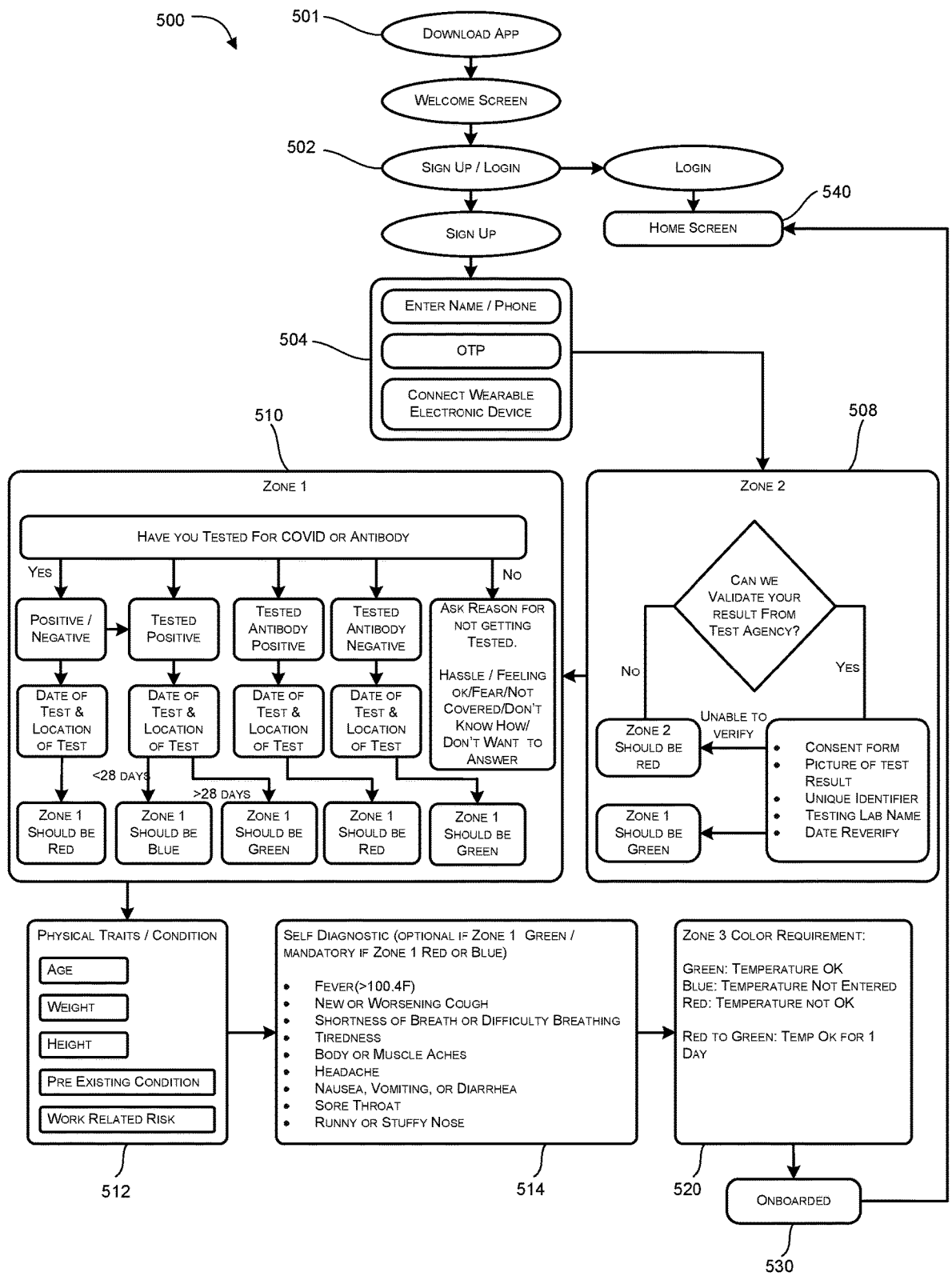
FIG. 5 illustrates an exemplary flow diagram of an application for sending/transmitting a status query to the centralized server, using an entity electronic device or a computing device, for indicating one or more health attributes of the first entity, in accordance with an embodiment herein.

FIG. 5, with reference to FIGS. 1 through 4, illustrates an exemplary flow diagram 500 of an application for sending/transmitting a status query to the centralized server 112, using an entity electronic device (102 or 107) or the computing device 110, for indicating one or more health attributes of the first entity, in accordance with an embodiment herein. The color examples described below and in the drawings are merely examples, and accordingly any color and/or color combination may be used in accordance with the embodiments herein. At 501, the application may be downloaded on the entity electronic device (102 or 107) or on the computing device 110 to provide a welcome screen with an option to sign up or login, as shown in 502. At 504, the entity electronic device (102 or 107) or the computing device 110 may provide the necessary information such as name or phone number associated with the entity (103 or 104) wearing the wearable electronic device 105, 106, 300, and the wearable electronic device 105, 106, 300 may be connected to the entity electronic device (102 or 107) or the computing device 110 using the communication interface, as discussed in previous embodiments. Upon successful login, at 508, zone 2 validation may occur first, wherein the zone 2 may be associated with a second illumination zone 322 on the wearable electronic device 105, 106, 300. A status query such as "Can we validate your result from test agency?" may be transmitted to the centralized server 112 from the entity electronic device (102 or 107) or the computing device 110. Based on the status information computed by the processors of the centralized server 112, the second illumination zone 322 (zone 2) may be illuminated as a red color if the answer is "no", or if the answer may be "yes", then information such as consent form, picture of result test, details of laboratory or date of testing may be retrieved and the second illumination zone 322 may be illuminated as a green color. In case if the verification may not be enabled due to any reason then the second illumination zone 322 may be illuminated as a red color. Based on the test results retrieved from the zone 2, a zone 1 validation may occur, wherein the zone 1 may be associated with first illumination zone 320 on the wearable electronic device 105, 106, 300. A status query such as "Have you tested for COVID or antibody?" may be transmitted to the centralized server 112 from the entity electronic device (102 or 107) or the computing device 110. Based on the status information computed by the processors of the centralized server 112, if the answer is "no", then various other queries may be generated related to the reasons of not getting tested, or if the answer may be "yes", then the first illumination zone 320 on the wearable electronic device 105, 106, 300 may be illuminated as a particular color based on the result of the test as shown in 510, wherein the date and location of the test may be easily accessed in each case. The following four test results may be obtained:

COVID test positive (<28 days): Zone 1—blue color
COVID test positive (>28 days): Zone 1—green color
Antibody test positive: Zone 1—red color
Antibody test negative: Zone 1—green color The application may also show physical traits or condition of the entity as shown in 512. Further, a self-diagnostic test as shown in 514, which may be obtained by manual entry on the entity electronic device (102 or 107) or by sensors 316 of the wearable electronic device 105, 106, 300, which may be optional if zone 1 may be green or compulsory if zone 1 may be red or blue in color. At 520, risk assessment of the pathogenic exposure to the one or more entities posed by the other entity, may be assessed in zone 3, wherein the zone 3 may be associated with the third illumination zone 324 on the wearable electronic device 105, 106, 300. In zone 3, one or more factors such as presence of temperature may be checked based on the updated information or self-diagnostic test, wherein the presence or absence of a fever or a selected temperature may be indicated as a different color on the wearable electronic device 105, 106, 300 as shown in 520. Once the unique alerts may indicate the status of health attributes of the entity (103 or 104) as safe or not risky to other entities then the entity (103 or 104) may be allowed to onboard 530, and the home screen 540 may be accessed. If the entity (103 or 104) has already been verified as stated above, then the home screen may be directly accessible upon providing a certain set of credentials to login.

Figure 6:
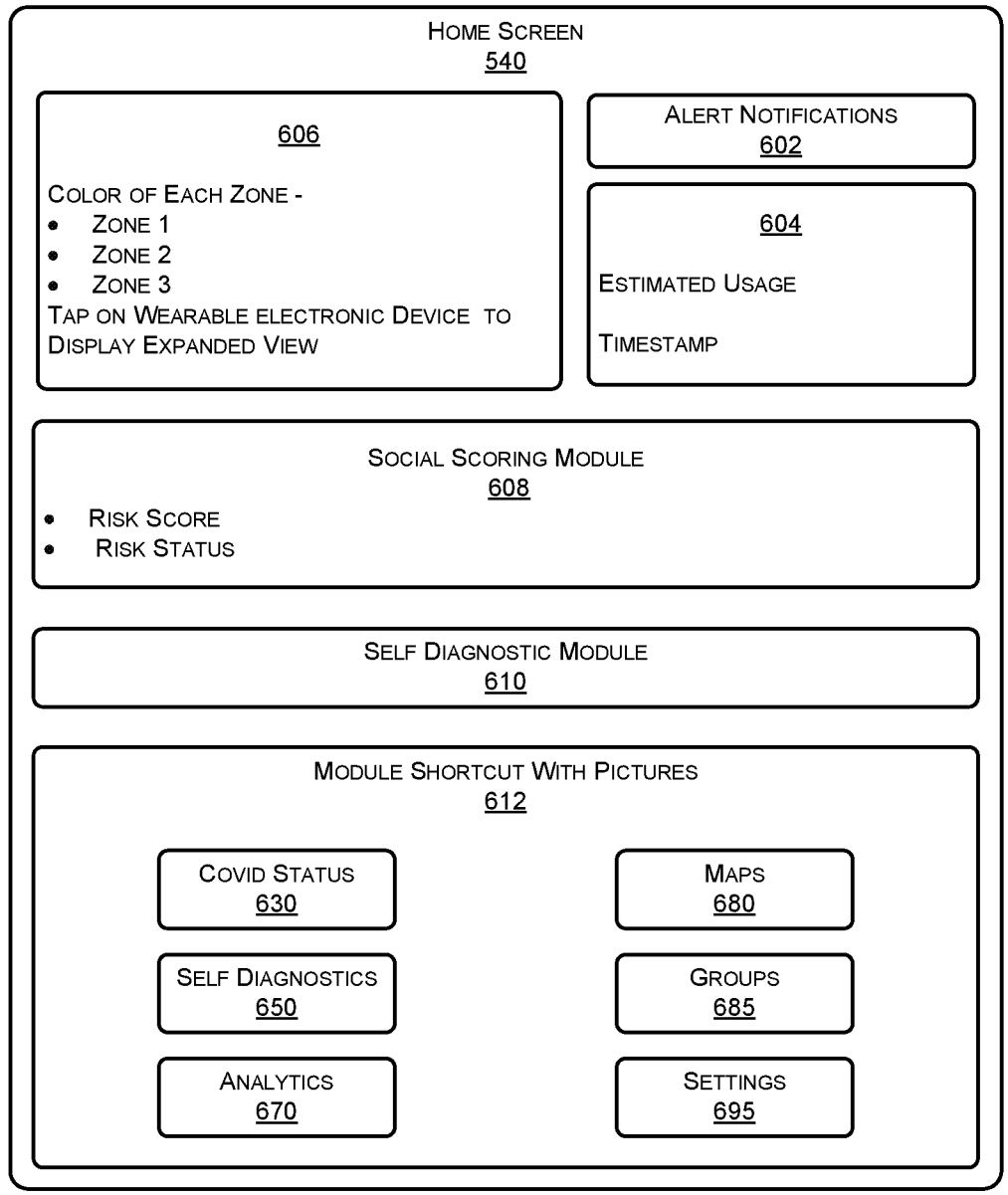
FIG. 6 illustrates an exemplary representation of the application home screen of FIG. 5 that may be accessed using the entity electronic device or a computing device, in accordance with an embodiment herein.

FIG. 6, with reference to FIGS. 1 through 5, illustrates an exemplary representation of an application home screen 540 of FIG. 5 that may be accessed using the entity electronic device (102 or 107) or the computing device 110, in accordance with an embodiment herein. The home screen 540 may include alert notification 602 for providing various updates to the entity or operator of the computing device 110. The color of each zone as displayed on the wearable electronic device 105, 106, 300 may also be shown in 606. The power source 314 (e.g., battery) status on the wearable electronic device 105, 106, 300 and last synced timestamp may be shown in 604. The home screen may also include a social scoring module 608 indicating the risk score and risk status information, wherein the risk score and risk status may be a number in the range from 1 to 100, and higher risk score may indicate greater risk to other entities whereas higher risk status may indicate greater risk to the entity wearing the wearable electronic device 105, 106, 300. The home screen may also include a self-diagnostics module 610 indicating the health status as healthy, unhealthy, or recovering. The home screen may also include a shortcut for other modules 612 such as COVID status 630, self-diagnostics 650, analytics 670, maps 680, groups 685, and other settings 695. The settings module 695 may enable to change one or more settings in the application or on the wearable electronic device 105, 106, 300.

Figure 7:
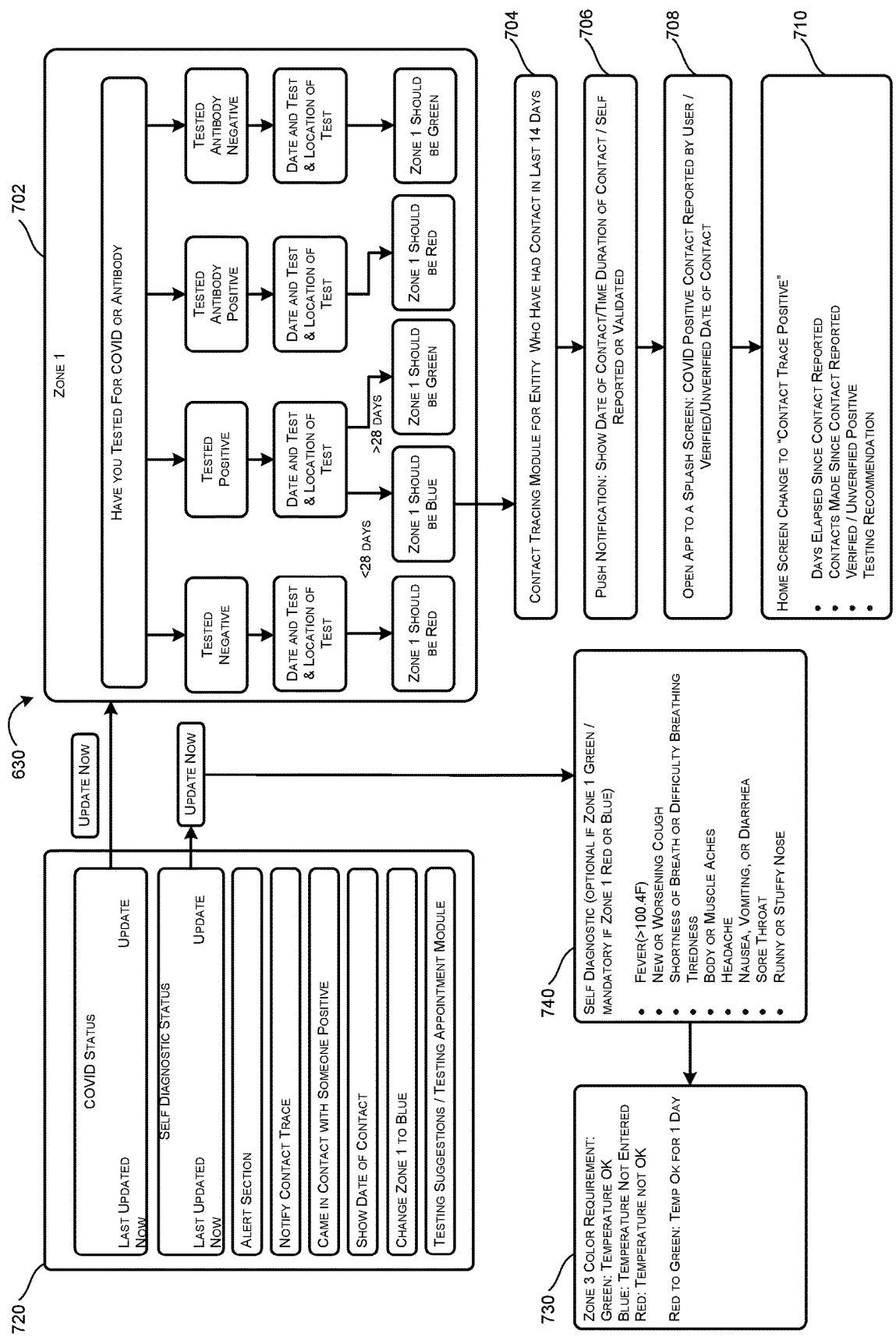
FIG. 7 illustrates an exemplary representation of the COVID status module of FIG. 6, in accordance with an embodiment herein.

FIG. 7, with reference to FIGS. 1 through 6, illustrates an exemplary representation of the COVID status module 630 of FIG. 6, in accordance with an embodiment herein. The COVID status module 630 may include COVID status 720 with last updated date, such that if not updated recently, then an update may be achieved as shown in 702, by transmitting a status query such as "Have you tested for COVID or antibody?" to the centralized server 112 from the entity electronic device (102 or 107) or the computing device 110, similar to that discussed in block 510 during onboarding. Based on the status information computed by the processors 202 of the centralized server 112, the COVID status in 720 may be updated. The COVID status module 630 may also enable contact tracing 704 if entity (103 or 104) may have tested positive. The contact tracing information may be obtained as push notification 706, with details related to the contact made, and further may also enable to track the days passed and other recommendations 710 by accessing a splash screen 708. The COVID status module 630 may further include self-diagnostic status in 720 with last updated date, such that if not updated recently, then may be achieved by a self-diagnostics check as shown in block 740 similar to that discussed in block 514 during onboarding. In an example, this may be obtained by manual entry on the entity electronic device (102 or 107) or by sensors 316 of the wearable electronic device 105, 106, 300, which may be optional if zone 1 may be green or compulsory if zone 1 may be red or blue in color. Further, the zone 3 color based on the presence or absence of temperature of entity (103 or 104) may also be updated as shown in 730, similar to that discussed in block 520 during onboarding.

Figure 8:
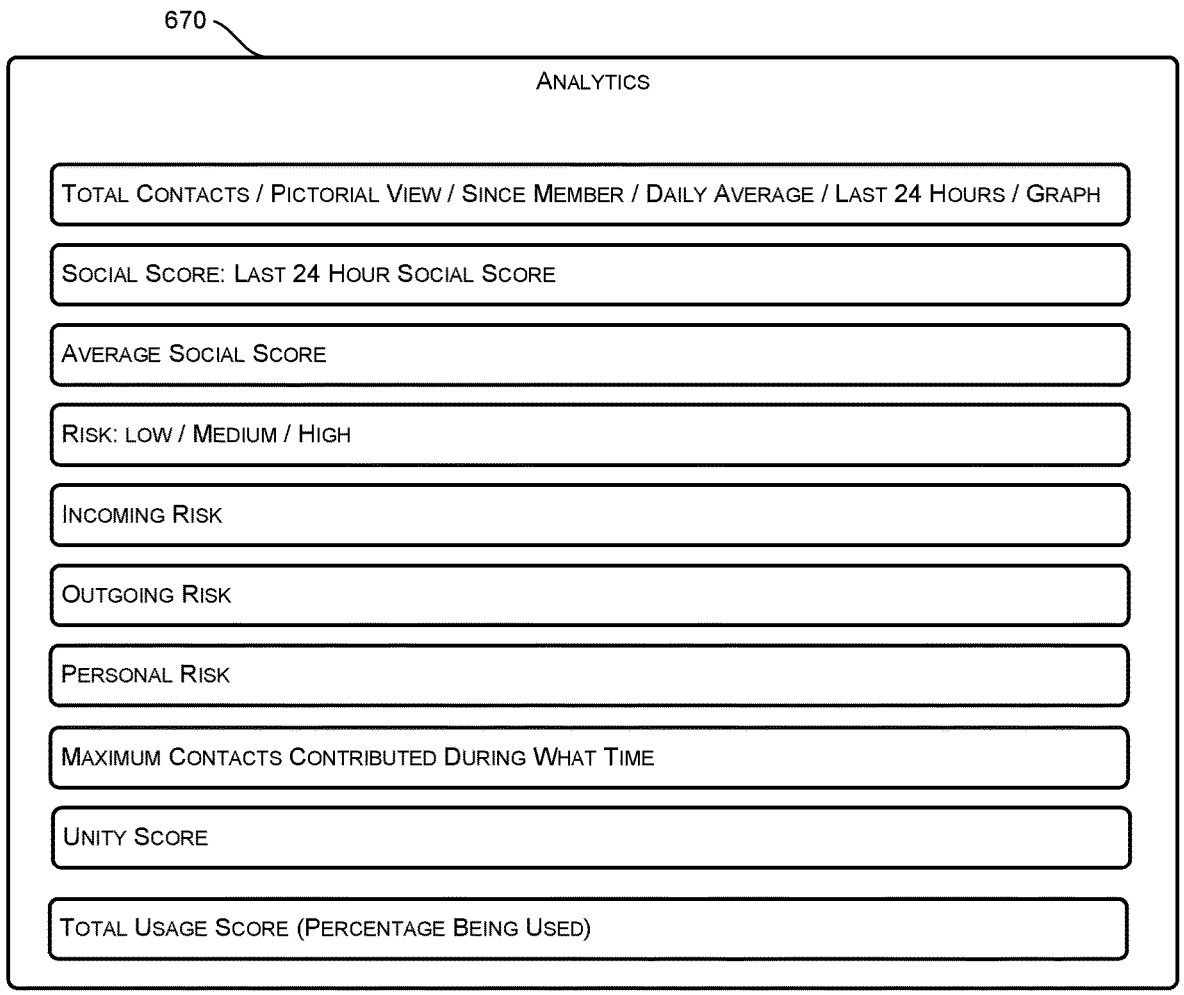
FIG. 8 illustrates an exemplary representation of the analytics module of FIG. 6, in accordance with an embodiment herein.

FIG. 8, with reference to FIGS. 1 through 7, illustrates an exemplary representation of the analytics module 670 of FIG. 6, in accordance with an embodiment herein. The analytics module 670 may include the status of the contacts, social score (social distancing score or direct social score), risk level, incoming risk (risk receivable score), outgoing risk (risk transferrable score), unity score or total usage score. In an exemplary embodiment, the analytics module may also exhibit any of:

Individual estimated R0 (Reproduction Number) based on Social attributes

Flattening of curve efforts via graph depiction

Efforts of people not infected via number and graph

Efforts of lives saved via number and graph.

In an embodiment, based on a score, any of the following may be implemented:

A point system may be developed based on risk factors, such as an entity with a good score may have more credits and may have ability to use common areas more freely.

Entry to social places may be controlled based on social score.

A daily quota of expendable points may be created based on risk factor, wherein the daily quota may be calculated based on personal risk factor and scaled based on predictive analysis, such that upon reaching the quota limit, an entity may be turned into a high-risk entity.

Enable habit formation by enabling entity to form better social distancing habits with daily progressive targets.

Figure 9:
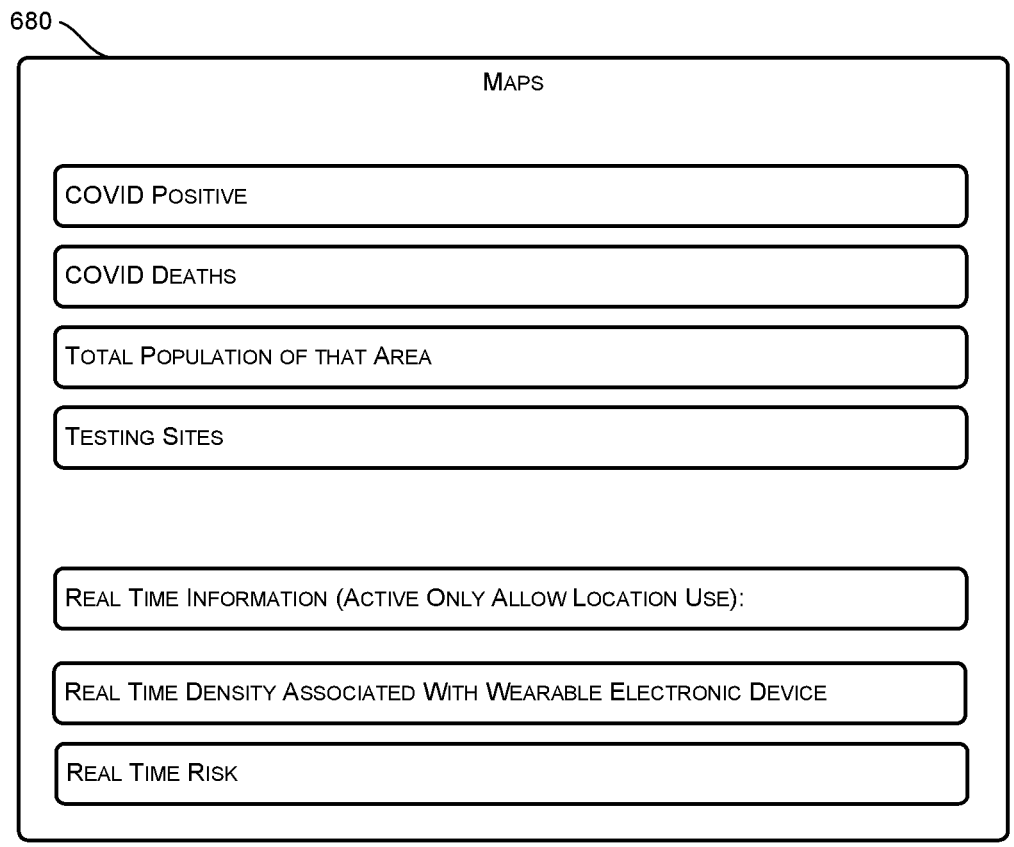
FIG. 9 illustrates an exemplary representation of the maps module of FIG. 6, in accordance with an embodiment herein.

FIG. 9, with reference to FIGS. 1 through 8, illustrates an exemplary representation of maps module 680 of FIG. 6, in accordance with an embodiment herein. The maps module 680 may include location-based statistics including the number of COVID infected positive cases, or death cases, overall population in the area, and testing sites. An access to real time information may be enabled if the entity has provided access to his/her location as well. Other information may include real time information such as real time density of people or real time risk posed to the entity in a particular area. In an exemplary embodiment, using the first entity electronic device 102, the first entity 103 may access maps feature that may provide the first entity 103 with any of the following information, in case of pandemic such as COVID:

Percentage capacity a certain point of interest may be occupied to, such as a grocery store Total risk factor of a certain point of interest (cumulative sum of total risk factor (TRF) of all users currently at the point of interest)

Visual display of riskiness of a specific area, or a point of interest via colors:
Red Zone: High Risk
Yellow Zone: Moderate Risk
Green Zone: Low Risk Advice to travel or to not travel to a specific area and defining minimum social distancing score and/or maximum TRF recommended.

Crowd sourced information for specific areas and points of interest showing risk traits in real time.

Points of interests, businesses and social areas may self-report their cleanliness status and how they are adhering to cleanliness guidelines set by national or government agencies.

Figure 10:
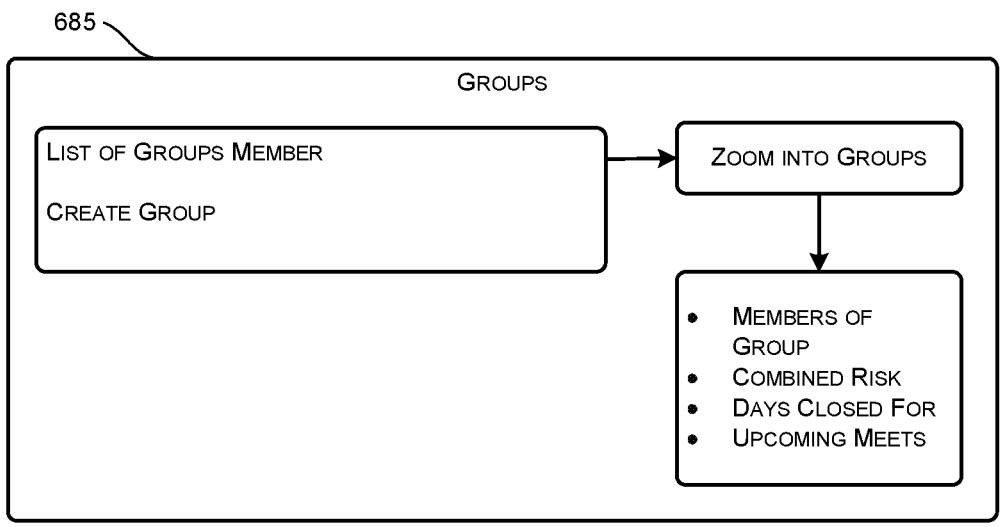
FIG. 10 illustrates an exemplary representation of the groups module of FIG. 6, in accordance with an embodiment herein.

FIG. 10, with reference to FIGS. 1 through 9, illustrates an exemplary representation of groups module 685 of FIG. 6, in accordance with an embodiment herein. The groups module 685 may be related to closed group tracking as discussed in previous embodiments, and may include details of members or entities of a closed group, as well as information related to the combined risk, number of days a group may be formed as a closed group, and upcoming meeting information.

The embodiments herein provide a wearable electronic device 105, 106, 300 to indicate one or more health attributes of a first entity to facilitate safe physical distancing between the first entity and one or more proximate entities for limiting pathogenic exposure. Moreover, the embodiments herein provide a device, system and method that enable individuals to safely access public places with reduced risk of pathogenic exposure, and with greater mental satisfaction. Furthermore, the embodiments herein provide a system and method to facilitate controlled access to facilities and services with intent to track pathogenic exposure, limit access to and manage interactions. Additionally, the embodiments herein may also be integrated with an external mobile application related to any of, but is not limited to, a transport service, a food delivery service, a social networking service, and a dating service.

The embodiments herein may be implemented entirely hardware, entirely software (including firmware, resident software, micro-code, etc.) or combining software and hardware implementation that may all generally be referred to herein as a "circuit," "module," "component," or "system." Furthermore, aspects of the embodiments herein may take the form of a computer program product comprising one or more computer readable media having computer readable program code embodied thereon.

Thus, it will be appreciated by those skilled in the art that the diagrams, schematics, illustrations, and the like represent conceptual views or processes illustrating systems and methods embodying the embodiments herein. The functions of the various elements shown in the figures may be provided through the use of dedicated hardware as well as hardware capable of executing associated software. Those skilled in the art further understand that the exemplary hardware, software, processes, methods, and/or operating systems described herein are for illustrative purposes and, thus, are not intended to be limited to any particular named component, system, device, or method.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Within the context of this document terms "coupled to" and "coupled with" are also used euphemistically to mean "communicatively coupled with" over a network, where two or more devices are able to exchange data with each other over the network, possibly via one or more intermediary device.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A wearable electronic device to indicate one or more health attributes of a first entity to facilitate safe physical distancing between the first entity and one or more proximate entities for limiting pathogenic exposure, the device comprising:

a housing to attach to the first entity;
   one or more sensors disposed in the housing and to sense the one or more health attributes of the first entity;
   a transceiver associated with an identifier tag and to enable communication of the one or more sensors with at least one of a first entity electronic device associated with the first entity and a computing device; and
   an indicator integrated with the housing to facilitate the safe physical distancing between the first entity and the one or more proximate entities for limiting pathogenic exposure therebetween by providing one or more unique alerts of the one or more health attributes of the first entity to the one or more proximate entities, wherein the one or more unique alerts indicate a status of the one of more health attributes,
   wherein the indicator comprises a light emitting diode (LED) indicator connected to the housing and is associated with one or more illumination zones on the housing to visually display the one or more unique alerts, and wherein each illumination zone is associated with the one or more health attributes of the first entity.

2. The device of claim 1, wherein the transceiver comprises a Bluetooth® low energy (BLE) transceiver, and wherein the identifier tag comprises any of a radio frequency identification (RFID) tag and Bluetooth® Low Energy (BLE) identifier.

3. The device of claim 1, wherein the one or more sensors comprise any of a pedometer, an accelerometer, light sensor, optical sensor, infrared sensor and a temperature sensor, and wherein the indicator comprises at least one of a visual indicator, a light indicator, a haptic indicator, and a sound indicator.

4. The device of claim 1, comprising a power source to power one or more electrical components of the wearable electronic device.

5. A system to manage safe physical distancing between a first entity and one or more proximate entities, the system comprising:

a wearable electronic device comprising:
      one or more sensors to sense one or more health attributes of the first entity;
      a transceiver to enable communication of the wearable electronic device with at least one of a first entity electronic device associated with the first entity and a computing device; and
   an indicator coupled to the one or more sensors and the transceiver to provide one or more unique alerts of the one or more health attributes of the first entity to the one or more proximate entities, wherein the one or more unique alerts indicate a status of the one of more health attributes, wherein the indicator comprises a light emitting diode (LED) indicator on the wearable electronic device, wherein the LED indicator is associated with one or more illumination zones on the wearable electronic device to visually display the one or more unique alerts, and wherein each illumination zone is associated with the one or more health attributes of the first entity;
   a centralized server comprising one or more processors coupled with a memory, the memory storing instructions which when executed by the one or more processors cause the system to:
      receive, from the first entity electronic device or the computing device, a first set of data packets related to a status query associated with the one or more health attributes of the first entity;

compute a status information, in response to the status query based on the one or more health attributes stored in a database of the centralized server, wherein the one or more health attributes is updated in the database using one or more inputs from any one of an external database and the first entity electronic device, wherein the first entity electronic device provides the inputs to the database based on a manual entry by the first entity or automatically through the one or more sensors of the wearable electronic device; and transmit to the first entity electronic device or the computing device, a second set of data packets related to the status information, in response to the status query; and one or more computing devices communicably coupled to centralized server, and to transmit, using a communication interface, to the wearable electronic device, the obtained status information from the centralized server, to actuate an indicator of the wearable electronic device, to provide one or more unique alerts to manage the safe physical distancing between the first entity and the one or more proximate entities for limiting pathogenic exposure therebetween.

6. A method for indicating one or more health attributes of a first entity on a wearable electronic device to facilitate safe physical distancing between the first entity and one or more proximate entities for limiting pathogenic exposure, the method comprising:

obtaining, using a computing device or a first entity electronic device associated with the first entity, an identity attribute associated with a wearable electronic device worn by the first entity;

authenticating, based on the obtained identity attribute, the first entity electronic device or the computing device, to access a database of a centralized server;

receiving, at the centralized server, from the first entity electronic device or the computing device, a first set of data packets related to a status query associated with the one or more health attributes of the first entity;

computing, at one or more processors of the centralized server, a status information, in response to the status query based on the one or more health attributes of the first entity stored in the database of the centralized server, wherein the one or more health attributes is updated in the database using one or more inputs from any one of an external database or the first entity electronic device, and wherein the first entity electronic device provides the inputs to the database of the centralized server, based on a manual entry in the first entity electronic device by the first entity or through one or more sensors of the wearable electronic device;

transmitting, by the one or more processors of the centralized server, to the first entity electronic device or the computing device, a second set of data packets related to the computed status information; and transmitting, from the first entity electronic device or the computing device, using a communication interface, to the wearable electronic device, the obtained status information associated with the one or more health attributes of the first entity, to actuate an indicator of the wearable electronic device, to provide one or more unique alerts of the one or more health attributes of the first entity to the one or more proximate entities, wherein the one or more unique alerts indicate a status of the one of more health attributes to facilitate the safe physical distancing between the first entity and the one or more proximate entities for limiting pathogenic exposure therebetween, wherein the one or more unique alerts are visually displayed on a light emitting diode (LED) indicator attached to the wearable electronic device to create one or more illumination zones on the wearable electronic device, and wherein each illumination zone is associated with the one or more health attributes of the first entity.

7. The method of claim 6, wherein the communication interface comprises a transceiver on the wearable electronic device, and the identity attribute comprises a Bluetooth® Low Energy (BLE) identifier associated with the transceiver, and wherein the authenticating is performed using a two-step authentication process.

8. The method of claim 7, comprising scanning a radio frequency identification (RFID) tag on the wearable electronic device to access a RFID code present therein for obtaining the Bluetooth® Low Energy (BLE) identifier associated with the transceiver.

9. The method of claim 6, wherein a first illumination zone of the one or more illumination zones indicates a first health attribute of the one or more health attributes, wherein the first health attribute comprises direct information related to a result of testing the first entity for checking pathogenic infection, wherein the result is selected from infected and active, infected and inactive, and non-infected, and wherein the testing is performed to check the pathogenic infection related to acute respiratory syndrome coronavirus 2 (SARS-CoV-2).

10. The method of claim 6, wherein a second illumination zone of the one or more illumination zones indicates a second health attribute of the one or more health attributes, wherein the second health attribute is obtained as the inputs from any of the manual entry by the first entity on the first entity electronic device or automatically through the one or more sensors of the wearable electronic device, and wherein the inputs are related to presence of a condition selected from fever, cough, shortness of breath, tiredness, body ache, muscle ache, headache, nausea, sore throat, and runny nose.

11. The method of claim 6, wherein a third illumination zone of the one or more illumination zones indicates a third health attribute of the one or more health attributes, and wherein the third health attribute is associated with a user profile data including a risk assessment of the pathogenic exposure to the first entity, risk assessment of the pathogenic exposure to the one or more proximate entities posed by the first entity, and an ability of the first entity to socialize with the one or more proximate entities with a minimum risk of the pathogenic exposure.

12. The method of claim 11, wherein the user profile data comprises physical attributes and social attributes, wherein the physical attributes comprise any of age, body weight, body height, pre-existing health condition and daily routine details, and wherein the social attributes include a record of interaction of the first entity with the one or more proximate entities, degree of contact of the first entity with the one or more proximate entities, distance travelled by the first entity from a home location to an outside location, a range of area covering maximum distance travelled over a time period around the home location, and wherein the social attributes is computed, by the one or more processors of the centralized server, to calculate at least one score selected from a social distancing score, a direct social score, a risk receivable score, a risk transferrable score, and a total risk factor score.

13. The method of claim 12, wherein the record of interaction of the first entity with the one or more proximate entities is updated on the first entity electronic device, wherein the record comprises a timestamp of the interaction and the distance sensed between the wearable electronic device worn by the first entity and a second wearable electronic device worn by the one or more proximate entities.

14. The method of claim 6, wherein the method facilitates safe physical distancing between a first group of entities comprising the first entity, and a second group comprising the one or more proximate entities, wherein the first group comprises a closed group and each member of the first group uses a separate wearable electronic device, wherein the first entity is allowed to interact with each member of the first group without the safe physical distancing, and wherein the method facilitates updating the database by tracking of the separate wearable electronic devices of the first group to record number of the members in the first group interacting with the first entity, duration of stay of the first entity in the first group without any interaction with the second group and health status information of each of the member in the first group.

15. The method of claim 6, wherein the method facilitates, using the one or more unique alerts, to enable alerting the first entity to maintain the safe physical distancing from the one or more proximate entities, alerting the first entity regarding frequency or duration of hand washing, alerting the first entity on face touching movement, and alerting the first entity based on location of movement, when approaching an area of relatively higher pathogenic exposure.

16. The method of claim 6, wherein the wearable electronic device of the first entity is to communicate, using the communication interface, with a third wearable electronic device worn by the one of the proximate entities and share the status information with each other, to visibly indicate the one or more health attributes.

17. The method of claim 6, wherein the wearable electronic device of the first entity is to maintain a record of interaction within a specified distance between the wearable electronic device of the first entity and wearable electronic devices of the proximate entities over a definite time duration to enable contact tracing.

18. The method of claim 6, wherein the wearable electronic device of the first entity, upon encountering a third wearable electronic device worn by one of the proximate entities, excites the third wearable electronic device, using the first entity electronic device or the computing device, to provide the one or more unique alerts associated with one or more health attributes of the proximate entity.

19. A non-transitory computer readable storage medium storing one or more sequences of instructions, which when executed by one or more processors, causes indicating one or more health attributes of a first entity on a wearable electronic device to facilitate safe physical distancing between the first entity and one or more proximate entities for limiting pathogenic exposure, by performing a method comprising:

receiving, at a centralized server, from a first entity electronic device associated with the first entity or a computing device, a first set of data packets related to a status query associated with the one or more health attributes of the first entity;

computing, at one or more processors of the centralized server, a status information, in response to the status query based on the one or more health attributes of the first entity stored in a database of the centralized server, wherein the one or more health attributes is updated in the database using one or more inputs from any one of an external database or the first entity electronic device; and transmitting, by the one or more processors of the centralized server, to the first entity electronic device or the computing device, a second set of data packets related to the status information, in response to the status query, wherein the obtained status information is transmitted from the first entity electronic device or the computing device, using a communication interface, to the wearable electronic device, the obtained status information associated with the one or more health attributes of the first entity, to actuate an indicator of the wearable electronic device, to provide one or more unique alerts of the one or more health attributes of the first entity to the one or more proximate entities, wherein the one or more unique alerts indicate a status of the one of more health attributes to facilitate the safe physical distancing between the first entity and the one or more proximate entities for limiting pathogenic exposure therebetween, wherein the one or more unique alerts are visually displayed on a light emitting diode (LED) indicator attached to the wearable electronic device to create one or more illumination zones on the wearable electronic device, and wherein each illumination zone is associated with the one or more health attributes of the first entity.

20. The computer readable storage medium of claim 19, wherein the method facilitates safe physical distancing between a first group of entities comprising the first entity, and a second group comprising the one or more proximate entities, wherein the first group comprises a closed group and each member of the first group uses a separate wearable electronic device, wherein the first entity is allowed to interact with each member of the first group without the safe physical distancing, and wherein the method facilitates updating the database by tracking of the separate wearable electronic devices of the first group to record number of the members in the first group interacting with the first entity, duration of stay of the first entity in the first group without any interaction with the second group and health status information of each of the member in the first group.

21. The computer readable storage medium of claim 19, wherein the method facilitates, using the one or more unique alerts, to enable alerting the first entity to maintain the safe physical distancing from the one or more proximate entities, alerting the first entity regarding frequency or duration of hand washing, alerting the first entity on face touching movement, and alerting the first entity based on location of movement, when approaching an area of relatively higher pathogenic exposure.

* * * * *